United States Patent
Song et al.

(10) Patent No.: US 11,923,049 B2
(45) Date of Patent: Mar. 5, 2024

(54) METHODS FOR PROCESSING NEXT-GENERATION SEQUENCING GENOMIC DATA

(71) Applicant: SOPHIA GENETICS S.A., Saint-Sulpice (CH)

(72) Inventors: Lin Song, Saint-Sulpice (CH); Tamara Steijger, Saint-Sulpice (CH); Jonas Behr, Saint-Sulpice (CH); Adam Novak, Saint-Sulpice (CH); David Hernandez, Saint-Sulpice (CH); Zhenyu Xu, Commugny (CH)

(73) Assignee: SOPHIA GENETICS S.A., Saint-Sulpice (CH)

( * ) Notice: Subject to any disclaimer, the term of this patent is extended or adjusted under 35 U.S.C. 154(b) by 1045 days.

(21) Appl. No.: 16/312,067

(22) PCT Filed: Jun. 19, 2017

(86) PCT No.: PCT/EP2017/064968
§ 371 (c)(1),
(2) Date: Dec. 20, 2018

(87) PCT Pub. No.: WO2017/220508
PCT Pub. Date: Dec. 28, 2017

(65) Prior Publication Data
US 2019/0206511 A1  Jul. 4, 2019

Related U.S. Application Data

(60) Provisional application No. 62/353,095, filed on Jun. 22, 2016.

(51) Int. Cl.
G16B 50/20 (2019.01)
G16B 20/20 (2019.01)
(Continued)

(52) U.S. Cl.
CPC .............. *G16B 50/20* (2019.02); *G16B 20/20* (2019.02); *G16B 30/00* (2019.02); *G16B 30/10* (2019.02);
(Continued)

(58) Field of Classification Search
CPC ........ G16B 50/20; G16B 30/10; G16B 20/20; G16B 30/00; G16B 50/00
(Continued)

(56) References Cited

U.S. PATENT DOCUMENTS 9,340,830 B2 * 5/2016 Lipson ................. C12Q 1/6827
2014/0282177 A1 9/2014 Wang
2015/0286495 A1 10/2015 Lee

OTHER PUBLICATIONS

PCT Search Report and IPER issued in PCT/EP2017/064968.

* cited by examiner

*Primary Examiner* — Larry D Riggs, II
*Assistant Examiner* — Guozhen Liu
(74) *Attorney, Agent, or Firm* — Bochner PLLC; Andrew D. Bochner

(57) ABSTRACT

A genomic data analyzer system method to analyze next generation sequencing genomic data from a sourcing laboratory. The method includes receiving, with a processor, a next generation sequencing analysis request from a sourcing laboratory, the next generation sequencing request comprising at least a raw next generation sequencing data file and the sourcing laboratory identification; identifying, with a processor, a first set of characteristics associated with the next generation sequencing analysis request, the first set of characteristics comprising at least a target enrichment technology identifier, a sequencing technology identifier, and a genomic context identifier; configuring, with a processor, a data alignment module to align the input raw sequencing data file in accordance with at least one characteristic of said
(Continued)

first set of characteristics; and aligning, with the data alignment module processor, the input sequencing data to a genomic sequence.

19 Claims, 9 Drawing Sheets

(51) Int. Cl.
*G16B 30/00* (2019.01)
*G16B 30/10* (2019.01)
*G16B 50/00* (2019.01)
G16B 20/00 (2019.01)
G16B 50/40 (2019.01)
G16B 50/50 (2019.01)

(52) U.S. Cl.
CPC .............. *G16B 50/00* (2019.02); *G16B 20/00* (2019.02); *G16B 50/40* (2019.02); *G16B 50/50* (2019.02)

(58) Field of Classification Search
USPC .......................................................... 702/20
See application file for complete search history.

```
Ref:     TGTGTGTG......TGTGTTTTTTTT
Read1:   TGTGTG--......TGTGTT-TTTTT
Read2:   TGTGTGTG......-TGTTTT-TTTT
Read3:   TGTGTG--......TGTGT-TTTTTT
Read4:   TG--TGTG......TGTGTTTTT-TT
Read5:   TGTGTG--......TGTGTTT-TTTT
Read6:   TGTGTGTG......TG--TTT-TTTT
Read7:   TGTGTGTG......--TGTTTTT-TT
Read8:   TGTGTG--......TGTGTTTT-TT
Read9:   TGTG--TG......TGTGT-TTTTTT
Read10:  TGTG--TG......TGTGT-TTTTTT
Read11:  TG--TGTG......TGTGTTT-TTTT
Read12:  TG--TGTG......TGTGTTTTT-T
Read13:  TGTGTGTG......TG--TTTT-TTT
Read14:  TGTGTGTG......--TGTTT-TTTT
Read15:  TGTGTGTG......--TGTT-TTTTT
```

FIG.7

```
Ref:    TGTGTGTG......TGTGTTTTTTTT
Read1:  TGTGTG--......TGTG-TTTTTTT
Read2:  TGTGTG--......TGTG-TTTTTTT
Read3:  TGTGTG--......TGTG-TTTTTTT
Read4:  TGTGTG--......TGTG-TTTTTTT
Read5:  TGTGTG--......TGTG-TTTTTTT
Read6:  TGTGTG--......TGTG-TTTTTTT
Read7:  TGTGTG--......TGTG-TTTTTTT
Read8:  TGTGTG--......TGTG-TTTTTTT
Read9:  TGTGTG--......TGTG-TTTTTTT
Read10: TGTGTG--......TGTG-TTTTTTT
Read11: TGTGTG--......TGTG-TTTTTTT
Read12: TGTGTG--......TGTG-TTTTTTT
Read13: TGTGTG--......TGTG-TTTTTTT
Read14: TGTGTG--......TGTG-TTTTTTT
Read15: TGTGTG--......TGTG-TTTTTTT
```

FIG. 8

False positive variant detection
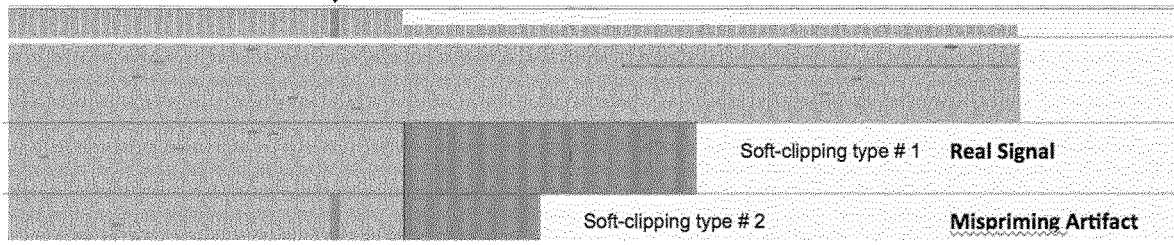
a)
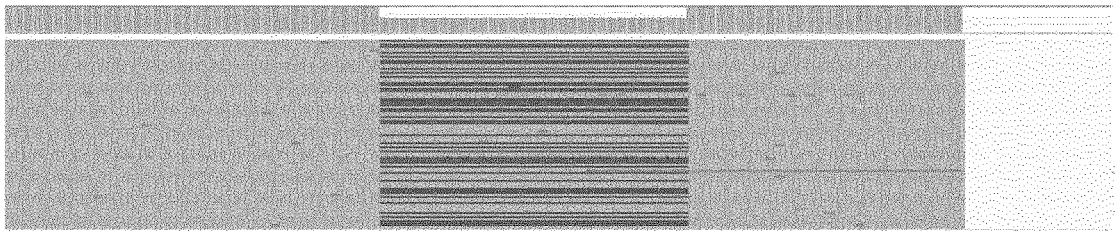
b)
FIG.9

METHODS FOR PROCESSING NEXT-GENERATION SEQUENCING GENOMIC DATA

FIELD OF THE INVENTION

Methods described herein relate to genomic analysis in general, and more specifically to next generation sequencing applications.

BACKGROUND OF THE INVENTION

Next-Generation Sequencing

Next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals (germline) or of cancerous tissues (somatic) can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference.

Targeted Enrichment

In some pathologies, a specific gene variant has been associated with the illness, such as the BRCA1 and BRCA2 genes in certain forms of hereditary breast and ovarian cancers or the CFTR gene in cystic fibrosis. Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR™ or the Illumina TruSeq® Amplicon assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent Sure Select™ Target Enrichment System, Roche NimbleGen SeqCap EZ, Illumina Nextera Rapid Capture, Agilent Haloplex™, and Multiplicom MASTR™.

In order to maximize the use of the massively-parallel processing NGS sequencer, a number of samples are multiplexed in the targeted NGS experiment—a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

Next Generation Sequencing Workflow Automation

Next Generation Sequencing (NGS) enables in particular to detect and report small changes ("variants") in the DNA sequence, such as single nucleotide polymorphisms (SNPs), insertions or deletions (INDELs), as compared to the reference genome, through bioinformatics methods such as sequencing read alignment, variant calling, and variant annotation. NGS workflows refer to the configuration and combination of such methods into an end-to-end genomic analysis application. In genomic research practice, NGS workflows are often manually setup and optimized using for instance dedicated scripts on a UNIX operating system, dedicated platforms including a graphical pipeline representation such as the Galaxy project, and/or a combination thereof. As clinical practice develops, NGS workflows may no longer be experimentally setup on a case-per-case basis, but rather integrated in SaaS (Software as a Service), PaaS (Platform as a Service) or IaaS (Infrastructure as a Service) offerings by third party providers. In that context, further automation of the NGS workflows is key to facilitate the routine integration of those services into the clinical practice.

One approach to NGS workflow automation, as described for instance in US2015/0286495 by IBM, consists in associating metadata fields to the genomic data. The data processing workflow may then be automatically operated in accordance with the metadata features such as for instance sample, processing site, laboratory, instrument, or assay characteristics. These features may be represented as key/value pairs having a structure or relationship such as conventionally represented in relational databases. As will be apparent to those skilled in the art, practical deployment of this method thus requires the various parties to agree on the metadata features to be associated with the genomic data on a case-per-case application basis, and these methods are therefore inherently limited to the automation of genomic workflow management based on explicit, structured metadata characteristics. One major limitation of this approach is the need to know in advance all the characteristics of any data that the data processing workflow may have to process, which makes it difficult to integrate the latest genomic discoveries and bioinformatics algorithms improvements in the genomic workflow. There is a need for more flexible workflows based on machine learning and/or artificial intelligence which can automatically adapt to the characteristics of the input data as part of their processing workflow.

Next Generation Sequencing Workflow Optimization

While next generation sequencing methods have been shown more efficient than traditional Sanger sequencing in the detection of SNPs and INDELs, their specificity (rate of true positive detection for a given genomic variant) and sensitivity (rate of true negative exclusion for a given genomic variant) may still be further improved in clinical practice. The specificity and sensitivity of NGS genomic analysis may be affected by a number of factors:

Biases introduced by the sequencing technology, for instance due to:
  Length of the reads relative to the length of the fragments;
  Too small number of reads (read depth);
  Errors or low quality bases introduced during sequencing;
  Inherent difficulties in counting homopolymer stretches, in particular with pyrosequencing (as in Roche 454 platforms) or semiconductor sequencing (as in Ion Torrent platforms), resulting in insertion and deletion errors;
Biases introduced by the DNA enrichment technology, for instance due to:
  Primers or probes non-specific binding, for instance due to storing the assay at a low temperature for too long, or due to too small amount of DNA in the sample;
  Introduction of sequence errors caused by imperfect PCR amplification and cycling, for instance due to temperature changes;
  Suboptimal design of the probes or primers. For example, mutations may fall within the regions of the probes or primers;
  Enrichment method limitations. For instance, long deletion may span the amplified region;
  Cross-contamination of data sets, read loss and decreased read quality due to fragment tagging with barcodes, adapters and various pre-defined sequence tags;
  Chimeric reads in long-insert pair-ended reading.
Biases introduced by the sample itself, for instance due to:
  Somatic features, in particular in cancer diagnosis based on tumor sample sequencing;
  The type of biological sample, e.g. blood, urine, saliva, and associated sample preparation issues, for instance causing degradation of DNA, contamination with alien DNA, or too low DNA input.
Biases introduced by the genomic data structure of certain regions specifically, for instance due to:
  High ratio of GC content in the region of interest;
  Presence of homopolymers, that is partial genomic sequence repetitions in certain regions causing ambiguities in initial alignment, and possibly inherent sequencing errors in particular with the Roche 454 and Ion Torrent sequencer technologies;
  Presence of homologous and low-complexity regions;
  Presence of non-functional pseudogenes that may be confused with functional genes, in particular in high-repeat genomic regions of the human genome when the DNA fragments are not long enough compared to the read length.

This limits the efficient deployment of NGS in routine genomic analysis applications, as a different genomic data analysis workflow need to be manually organized and configured with different sets of parameters by highly specialized personnel for each application to meet the clinical expectations in terms of specificity and sensitivity. The automation of genomic data processing workflows is particularly challenging as the workflows need to take into account the specific data biases introduced by the upstream NGS biological processes on the one hand and the genomic data structures inherent to the current application on the other hand. In early deployment of genomic testing, a limited number of tests and setups were processed by dedicated platforms, which could be manually setup, configured and maintained by highly skilled specialized staff. This approach is costly and does not scale well as more and more tests have to be conducted in daily operation by a single multi-purpose genomic analysis platform.

There is therefore a need for a better solution to automatize the genomic data processing workflows for data-driven medical applications, so that the same genomic data processing platform may operate on a diversity of genomic data as may be generated from different next-generation sequencing laboratory setups and in different genomic data contexts while optimizing the specificity and the sensitivity of the results to improve research and clinical practice over the prior art methods.

BRIEF SUMMARY

The foregoing advantages may be achieved by a method to analyze next generation sequencing genomic data from a sourcing laboratory, comprising:
  receiving, with a processor, a next generation sequencing analysis request from a sourcing laboratory, the next generation sequencing request comprising at least a raw next generation sequencing data file and the sourcing laboratory identification;
  identifying, with a processor, a first set of characteristics associated with the next generation sequencing analysis request, the first set of characteristics comprising at least a target enrichment technology identifier, a sequencing technology identifier, and a genomic context identifier;
  configuring, with a processor, a data alignment module to align the input raw sequencing data file in accordance with at least one characteristic of said first set of characteristics;
  aligning, with the data alignment module processor, the input sequencing data to a genomic sequence.

In a possible embodiment, the proposed genomic data analysis method may further comprise:
  configuring, with a processor, a variant calling module to detect variants associated with the input sequencing data in accordance with at least one characteristic of said first set of characteristics;
  detecting genomic variants, with the variant calling module processor, in the aligned genomic sequence;
  reporting, with a processor, the detected genomic variants to the sourcing laboratory.

In a further possible embodiment, the proposed genomic data analysis method may further comprise:
  identifying, with a processor, a second set of characteristics associated with the alignment data from the raw alignment data file, the second set of characteristics comprising at least a data alignment pattern identifier;
  configuring, with a processor, the data alignment module to refine at least one subset of the input raw sequencing data in accordance with at least one characteristic of the first set of characteristics and at least one characteristic of the second set of characteristics;

refining with the configured data alignment module processor, the subset of the input raw alignment data to produce a refined alignment data file.

In a possible embodiment, refining the subset of the input raw alignment data may comprise re-aligning a subset of the raw alignment data file. In another possible embodiment, refining the subset of the input raw alignment data may comprise extracting a subset of the raw alignment data file, refining this subset, and merging the resulting re-alignment data file with the raw alignment data file to produce the refined alignment data file.

In a possible embodiment, the proposed genomic data analysis method may further comprise:
  configuring, with a processor, a variant calling module to detect variants associated with the refined alignment data in accordance with at least one characteristic of the first set of characteristics and one characteristic of the second set of characteristics;
  detecting genomic variants, with the configured variant calling module processor, in the refined alignment data;
  reporting, with a processor, the detected genomic variants to the sourcing laboratory.

In a possible embodiment, the proposed genomic data analysis method may further comprise:
  identifying, with a processor, a third set of characteristics associated with the alignment data from the refined alignment data file, the third set of characteristics comprising at least a genomic context identifier;
  configuring, with a processor, a variant calling module to detect variants associated with the refined alignment data in accordance with at least one characteristic of the first set of characteristics, at least one characteristic of the second set of characteristics, and at least one characteristic of the third set of characteristics;
  detecting genomic variants, with the configured variant calling module processor, in the refined alignment data.

In a possible embodiment the proposed genomic data analysis method may further comprise reporting, with a processor, the detected genomic variants to the sourcing laboratory. In an alternate embodiment, the proposed genomic data analysis method may further comprise:
  identifying, with a processor, a fourth set of characteristics associated with the detected genomic variants, the fourth set of characteristics comprising at least a variant calling refinement identifier;
  configuring, with a processor, the variant calling module to detect variants associated with the refined alignment data in accordance with at least one characteristic of the first set of characteristics, at least one characteristic of the second set of characteristics, at least one characteristic of the third set of characteristics and at least one characteristic of the fourth set of characteristics;
  detecting refined genomic variants, with the configured variant calling module processor, in the refined alignment data and the detected genomic variants, to produce a refined set of genomic variants;
  reporting, with a processor, the refined set of genomic variants to the sourcing laboratory.

BRIEF DESCRIPTION OF THE DRAWINGS

FIG. 7 illustrates a mismatched genomic sequence alignment as may result from a standard alignment algorithm on next generation sequencing reads whereas FIG. 8 illustrates the proper genomic sequence alignment as may result from an optimized alignment algorithm on the same set of next generation sequencing reads, in an exemplary complex genomic sequence context characterized by multiple TG and TT repeats.

FIG. 9a) illustrates a false positive variant detection as may result from a standard alignment algorithm on next generation sequencing reads, whereas FIG. 9b) illustrates the proper genomic sequence alignment without the false positive variant detection as may result from an optimized alignment algorithm on the same set of next generation sequencing reads, in an exemplary next generation sequencing target enrichment technology context characterized by challenging soft clipping patterns.

DETAILED DESCRIPTION

Next Generation Sequencing Analysis System

Figure 1:
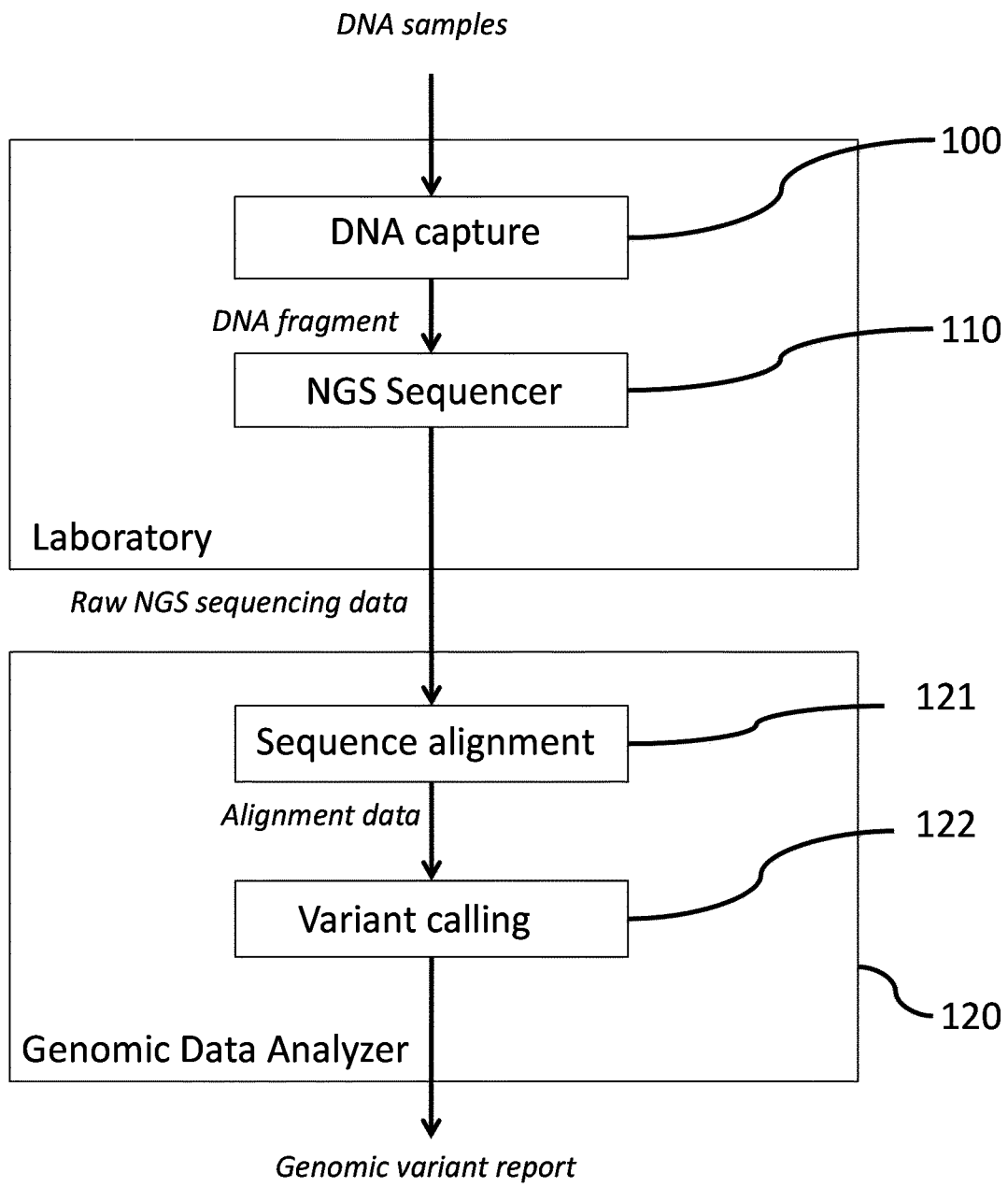
FIG. 1 represents a prior art next generation sequencing system.

FIG. 1 shows an exemplary genomic analysis system comprising a DNA enrichment assay 100, a next generation sequencer 110 and a genomic data analyzer 120.

In a NGS laboratory, a pool of DNA samples is processed by the DNA enrichment assay 100 to generate a library of pooled amplicons (for amplicon-based enrichment) or fragments (for probe-based enrichment) as DNA fragments input to the next generation sequencer 110, each set of amplicons/fragments corresponding to a different sample. The number of amplicons/fragments is application dependent. In some genomic analysis experiments, target enrichment may require 150 primers to enrich 75 different regions to be targeted out of the sample genome, resulting in a set of 75 amplicons for each sample. The number of samples may also be adapted to the next-generation sequencing sequencer 110 parallel processing capability, for instance 48 samples in the form of a library of pooled amplicons may be sequenced in parallel by an Illumina MiSeq sequencer.

Other NGS sequencer technologies may be used, such as for instance the Roche454™ GS Junior or GS FLX, Illumina MiSeq®, or Life Technologies Ion PGM™ sequencers.

The next-generation sequencer 110 analyses the input samples and generates sequence reads in a computer-readable file format representing raw NGS sequencing data. Depending on the NGS technology, one or more files may be output by the NGS sequencer 110. In some embodiments, for instance with Illumina sequencers, the FASTQ file format may be used with two different files for forward and reverse reads or as a single joined file. This text file typically starts with a sequence header marked by a '@' start character, followed by one line of sequence information represented as a string of 'A', 'T', 'C', 'G' nucleotide characters, then by a quality header marked by a '+' start character, followed by one line of quality metrics, one quality score matching each nucleotide read. The format for the quality metrics for each nucleotide in the sequence information string may depend on the sequencer. Some legacy sequencers output the raw sequencing data in the SFF (Standard Flowgram Format) binary file format, which comprises an informative header and the read data. Other embodiments are also possible, for instance some legacy Roche sequencers output multiple FASTQ files for a single patient analysis, while other sequencers, for instance the Ion Torrent PGM sequencers, have migrated to the compressed unmapped BAM file format, as may be recognized from the .basecallerbam file extension. As known to those skilled in the art of communication systems, the laboratory operates a computing infrastructure to store the resulting raw NGS sequencing data file in a laboratory biobank. The laboratory computing infrastructure connects, with authentication credentials, through a communication network, to the genomic data analyzer 120 and transmits a genomic analysis request comprising the raw NGS sequencing file to the genomic data analyzer 120.

The genomic data analyzer 120 computer system (also "system" herein) 120 is programmed or otherwise configured to implement different genomic data analysis methods, such as receiving and/or combining sequencing data and/or annotating sequencing data.

The genomic data analyzer 120 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. Examples of genomic data analyzer computing systems, environments, and/or configurations include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and the like. In some embodiments, the computer system may comprise one or more computer servers, which are operational with numerous other general purpose or special purpose computing systems and may enable distributed computing, such as cloud computing, for instance in a genomic data farm. In some embodiments, the genomic data analyzer 120 may be integrated into a massively parallel system. In some embodiments, the genomic data analyzer 120 may be directly integrated into a next generation sequencing system.

The genomic data analyzer 120 computer system may be adapted in the general context of computer system-executable instructions, such as program modules, being executed by a computer system. Generally, program modules may include routines, programs, objects, components, logic, data structures, and so on that perform particular tasks or implement particular abstract data types. As is well known to those skilled in the art of computer programming, program modules may use native operating system and/or file system functions, standalone applications; browser or application plugins, applets, etc.; commercial or open source libraries and/or library tools as may be programmed in Python, Biopython, C/C++, or other programming languages; custom scripts, such as Perl or Bioperl scripts.

Instructions may be executed in distributed cloud computing environments where tasks are performed by remote processing devices that are linked through a communications network. In a distributed cloud-computing environment, program modules may be located in both local and remote computer system storage media including memory storage devices.

As illustrated on FIG. 1, the genomic data analyzer 120 may comprise a sequence alignment module 121, which compares the raw NGS sequencing data to a reference genome. The sequence alignment module 121 may be configured to execute different alignment algorithms. Standard raw data alignment algorithms such as Bowtie2 or BWA that have been optimized for fast processing of numerous genomic data sequencing reads may be used, but other embodiments are also possible. The alignment results may be represented as one or several files in BAM or SAM format, as known to those skilled in the bioinformatics art, but other formats may also be used, for instance compressed formats or formats optimized for order-preserving encryption, depending on the genomic data analyzer 120 requirements for storage optimization and/or genomic data privacy enforcement.

The resulting alignment data may be further filtered and analyzed by a variant calling module 122 to retrieve variant information such as SNP and INDEL polymorphisms. The variant calling module 122 may be configured to execute different variant calling, variant annotation, variant prioritization and/or variant classification algorithms. Resulting detected variant information may then be output by the genomic data analyzer module 120 as a genomic variant report for further processing by the end user, for instance with a visualization tool, and/or by a further variant annotation processing module (not represented).

Figure 2:
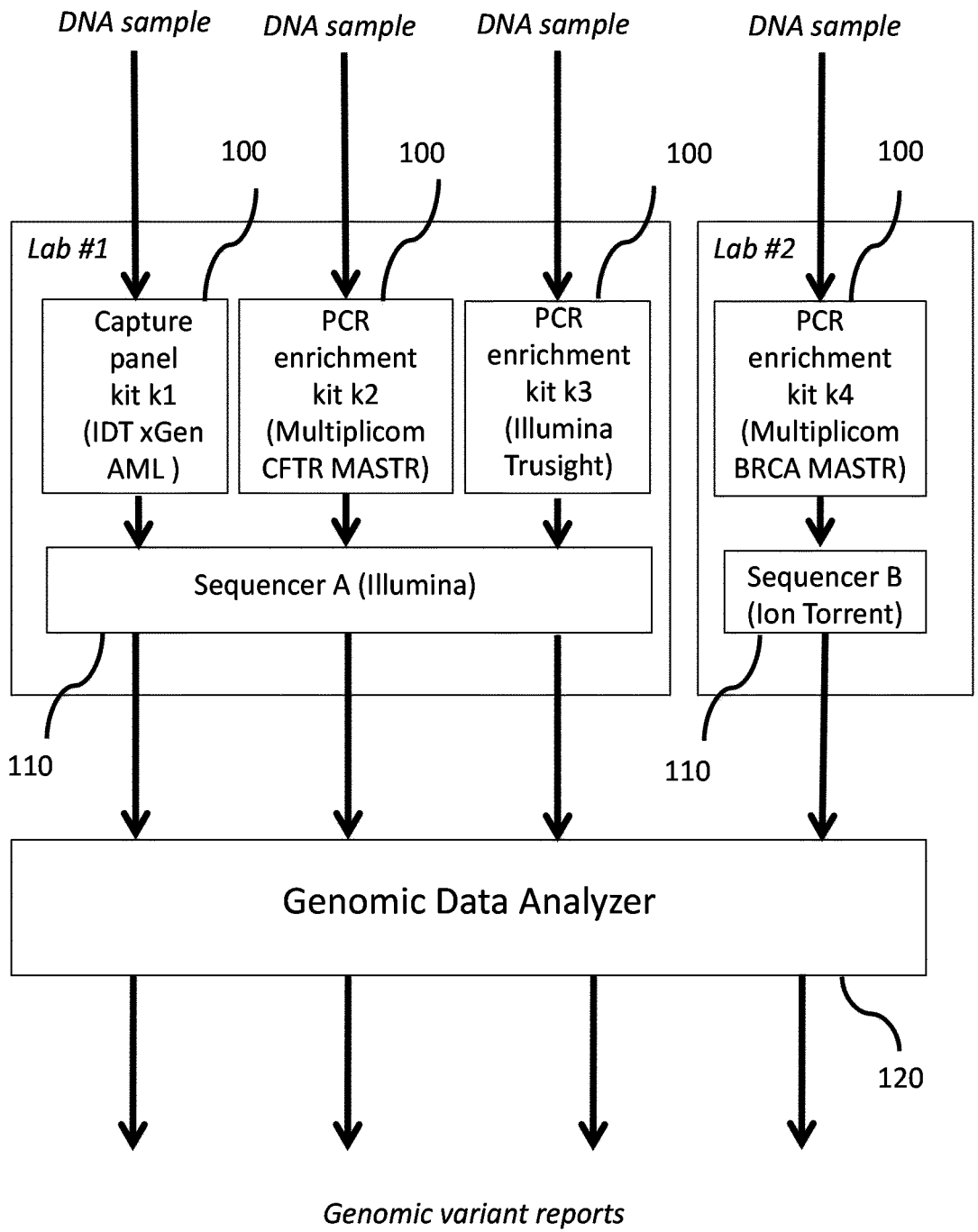
FIG. 2 illustrates a single genomic data analyzer system automatically operating on multiple next generation sequencing data inputs from a plurality of sourcing laboratories.

In a preferred embodiment of the present disclosure, the genomic data analyzer 120 may be adapted to automatically detect, with a processor, a set of characteristics that uniquely determine the input sequencing data and corresponding genetic context, the DNA enrichment context such as the sample type or laboratory process characteristics, the DNA enrichment technology such as the targeted enrichment target kit or capture probe assay characteristics, and/or the NGS sequencing technology. As will be apparent to those skilled in the art of next generation sequencing, these experimental characteristics may cause specific biases in the sequence alignment and/or the variant calling results. FIG. 2 shows an illustrative example of a genomic data analyzer 120 adapted to automatically process next generation sequencing data from a couple of different experimental setups and genomic contexts. For instance, a first laboratory Lab #1 may be equipped with a next generation sequencer A 110 manufactured by Illumina, which typically outputs two files in the FASTQ format, one for forward reads and one for reverse reads of the genomic data sequences. During a single day of operation, Lab #1 may use the same genomic data analyzer platform 120 to routinely analyze germline variants as well as somatic variants from various biological samples, such as blood, saliva or urine samples. Different genomic analysis assays for DNA enrichment 100 may be used accordingly upfront the sequencer, such as for instance:

Kit #k1: The Integrated DNA Technologies xGen® AML Cancer Panel v1.0. This panel of over 10000 xGen Lockdown® probes provides targeted enrichment for more than 260 genes to detect human genome mutations associated with Acute Myeloid Leukemia (AML).

Kit #k2: The Multiplicom CFTR MASTR™ Dx assay. This assay is dedicated to the detection, with a multiplex amplification technology, of the CFTR gene mutations causing cystic fibrosis.

Kit #k3: The Illumina® Trusight® Myeloid Panel. This panel applies DNA amplification to target 54 genes associated with mutations frequently causing myeloid malignancies.

In parallel, a second laboratory Lab #2 may offer a similar next generation sequencing service on the same or different pathologies, possibly with different technologies. Lab #2 may for instance employ a different target enrichment technology kit #k4, such as the BRCA MASTR™ Dx Plus assay by Multiplicom. This amplicon-based enrichment assay is dedicated to the detection of gene mutations associated with certain forms of hereditary breast and ovarian cancers. Lab #2 may also use a different sequencer B 110, for instance an Ion Torrent sequencer, which outputs an unmapped BAM file with raw NGS reads and quality information.

The proposed genomic data analyzer system 120 may thus serve next generation sequencing genomic analysis requests from different labs such as Lab #1 and Lab #2 that are independently operating different sequencer technologies A and B 110 and different DNA enrichment technologies #k1, #k2, #k3, #k4 100 on different samples for different genes. The proposed genomic data analyzer system 120 may automatically detect a set of characteristics from the input data and requests received from the laboratory and may adapt the configuration of the sequence alignment module 121 and the variant calling module 122 accordingly, without requiring a time consuming and costly manual setup to minimize the data biases possibly induced by each different biological workflow. The example of FIG. 2 and the above listed kits and sequencer technologies are illustrating four different experimental paths for the sake of simple illustration only; as will be apparent to those skilled in the art, there may be dozens or even hundreds of different clinical laboratory setups for multiple sourcing laboratories operating with the same genomic analyzer 120, and this number and diversity is likely to further increase with the deployment of additional technologies and assays as the NGS-based personalized medicine clinical practice develops.

In an embodiment of the present disclosure, the genomic data analyzer 120 may automatically derive information from the sourcing laboratory identification, as some laboratories may be operating only certain technologies and certain genomic analyses. In a possible embodiment, the genomic data analyzer 120 may thus further comprise a laboratory information database listing the sequencer technologies, the target enrichment technologies and/or the genomic targets associated with the sourcing laboratory identification. The genomic data analyzer 120 may configure the laboratory information database at the time of registering a new laboratory interface to the genomic data analyzer 120. The genomic may further configure the laboratory information database at the time of updating an already registered laboratory interface to the genomic data analyzer 120, for instance when the sourcing laboratory deploys a new technology and/or a new test. The genomic data analyzer 120 may also register detailed information associated with the target enrichment technology, such as the genomic sequence patterns of the target enrichment primers, in the laboratory information database and/or in dedicated laboratory metadata files associated with the target enrichment identifiers in the laboratory information database (for instance with an hyperlink or a filename). The metadata files may be in text format and in particular in the BED format known to those skilled in the art of bioinformatics, but other embodiments are also possible.

In an embodiment of the present disclosure, depending on the detected genomic experiment characteristics, the genomic data analyzer 120 may configure the sequence alignment module 121 to operate additional data processing steps and/or use different sets of configuration parameters such that the data biases caused by the genomic experiment characteristics are minimized.

In another embodiment of the present disclosure, depending on the detected input characteristics, the genomic data analyzer may configure the variant calling module 122 to operate additional data processing steps and/or use different sets of configuration parameters such that the data biases caused by the genomic experiment characteristics are minimized.

In a further embodiment of the present disclosure, depending on the results of the initial sequence alignment by the sequence alignment module 121, the genomic data analyzer 120 may be further adapted to identify next generation sequencing data alignment biases that become apparent when analyzing the alignment data. The genomic data analyzer may accordingly configure the sequence alignment module 121 to execute an additional step of re-alignment of the raw NGS sequencing data. This re-alignment may be constrained by additional parameters as may be determined from the initial alignment results. In a possible embodiment the re-alignment is applied specifically on a sub-region of the genomic sequence. The resulting re-alignment data may be further filtered and analyzed by the variant calling module 122 to output a more relevant genomic variant report with increased sensitivity and specificity for variant detection.

In a further embodiment of the present disclosure, depending on the results of the variant calling by the variant calling module 122, the genomic data analyzer 120 may be further adapted to identify variant calling biases that become apparent when calling variants on the alignment data. The genomic data analyzer may accordingly configure the variant calling module 122 to execute an additional step of re-calling variants on all or part of the alignment data. This refined variant calling step may be constrained by additional parameters as may be determined from the former alignment and variant calling results. In a possible embodiment variants are specifically called on a subset of the aligned genomic data. The resulting refined variant calling data may be further combined with the standard variant calling results by the variant calling module 122 to output a more relevant genomic variant report with increased sensitivity and specificity for variant detection. In a possible embodiment, some variant calling results may be excluded from the genomic variant report as identified possibly biased by the variant calling module 122, so that a more relevant genomic variant report is generated by the genomic data analyzer 120 with increased sensitivity and specificity for variant detection.

The generic, multi-purpose genomic data analyzer 120 thus facilitates the analysis and reporting of multiple different genomic variants from raw next generation sequencing data received from a diversity of clinical setups operated by multiple sourcing laboratories without requiring dedicated manual configuration or exhaustive metadata definition and documentation to adapt to each combination of biological setup and diagnosis context for each clinical analysis.

NGS Sequencing Analysis Workflow

Figure 3:
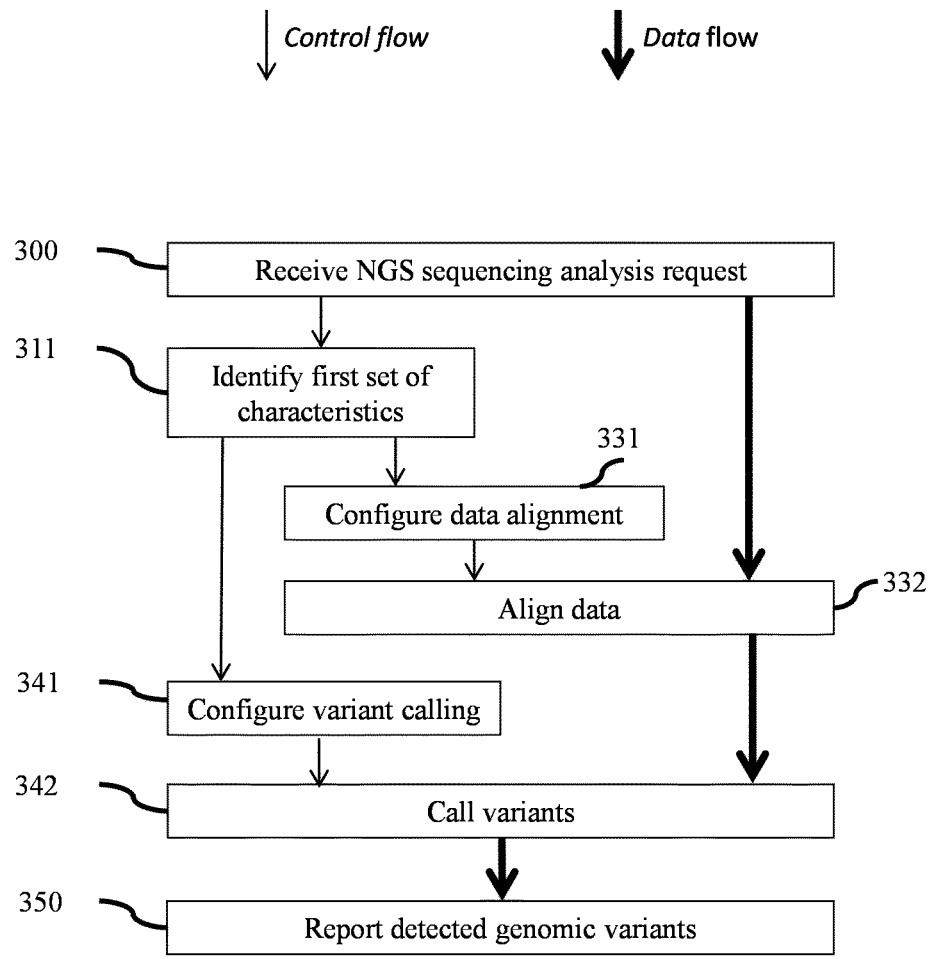
FIG. 3 shows the flowchart of a next generation sequencing genomic analysis workflow according a possible embodiment of the disclosure.

FIG. 3 shows a possible embodiment of a genomic data analysis method, comprising:
receiving 300 a next generation sequencing analysis request;
identifying 311 a first set of characteristics associated with the next generation sequencing analysis request, the first set of characteristics comprising at least a target enrichment technology identifier, a sequencing technology identifier, and a gene context identifier;

configuring 331 a data alignment module 121 to align the input sequencing data in accordance with at least one characteristic of said set of characteristics;

aligning 332, with the data alignment module 121, the input sequencing data to a genomic sequence;

configuring 341 a variant calling module 122 to identify variants associated with the input sequencing data in accordance with at least one characteristic of said set of characteristics;

identifying 342 genomic variants, with the variant calling module 122, in the aligned genomic sequence;

reporting 350 detected genomic variants.

The next generation sequencing analysis request comprises at least a raw next generation sequencing data file. The genomic data analyzer 120 may automatically extract information about the NGS experiment from this raw NGS data file structure, for instance:
  the file format and possibly some file header information;
  the length of the reads;
  the presence of adaptors that are specific to an enrichment or sequencing technology.
  the number of the reads, as indicated for instance in the header of the SFF file format;
  the quality range of the reads;
  the presence of primer patterns associated with a specific target enrichment technology and gene context.

The genomic data analyzer 120 may also automatically derive further information from the sourcing laboratory identification associated with the next generation sequencing analysis request, by looking up into the laboratory information database listing the sequencer technologies, the target enrichment technologies and/or the genomic analysis tests associated with the sourcing laboratory identification. The genomic data analyzer 120 may automatically identify the sourcing laboratory from its authentication credentials, but other embodiments are also possible, for instance the next generation sequencing request may further comprise metadata information such as a laboratory identifier and the genomic data analyzer 120 may directly identify the sourcing laboratory from reading the laboratory identifier in the NGS request metadata.

The genomic data analyzer 120 may accordingly identify 311, from the information extracted from the raw NGS data file structure and the sourcing laboratory identification, a first set of characteristics associated with the next generation sequencing analysis request, such as:
  The sequencer technology identifier;
  The target enrichment technology identifier;
  The genomic context identifier.

The genomic data analyzer 120 may thus automatically configure 331 the data alignment module 121 to execute data alignment 332 on the raw next generation sequencing data in accordance with at least one characteristic of the first set of characteristics, such as for instance the sequencer technology identifier. The genomic data analyzer 120 may further automatically configure 341 the variant calling module 122 to execute variant calling 342 on the resulting alignment data, in accordance with at least one characteristic of the first set of characteristics, such as for instance the genomic context identifier.

While some of the genome analysis characteristics may be directly identified from the input data structures, some further data biases may only be identified after a first attempt to align the input data to a genomic sequence reference. In a possible embodiment, the genomic data analyzer 120 may automatically extract a second set of characteristics information corresponding to the target enrichment technology context from the presence of certain specific sub-sequence patterns in the raw aligned data, for instance:
  soft clipped reads after alignment.
  primer patterns to be trimmed out of the alignment data, for amplicon-based target enrichment technologies;
  assay-dependent patterns specific to amplicon-based target enrichment technology primer design, such as for example, miss-priming patterns, primer dimmers, etc.

This information may enable the genomic data analyzer to identify a data alignment pattern characteristic identified, which is only available after alignment 332, and which indicates whether certain regions in the raw data may contain potentially missed variants or are subject to specific biases, due to the sequencing and/or the enrichment technology. For instance, the conventional raw alignment algorithms Bowtie2 or BWA have been optimized for possibly parallel processing of large NGS data by processing independently each read mapping, without considering all the reads that mapped to the same regions together, but relevant mutation information may still be identified in the remaining unmapped reads by using more specific alignment algorithms. The genomic data analyzer may accordingly configure the sequence alignment module 121 to execute a few additional steps to refine the raw alignment data file. As will be apparent to those skilled in the art of bioinformatics, these operations may include for instance:
  re-aligning the reads in a certain region;
  assigning the reads to different amplicons;
  conducting primer trimming of the amplicon-based enrichment technology;
  marking/trimming the mis-primmed reads;
  unifying the representation of the variants in the raw alignment file, etc.

Figure 4:
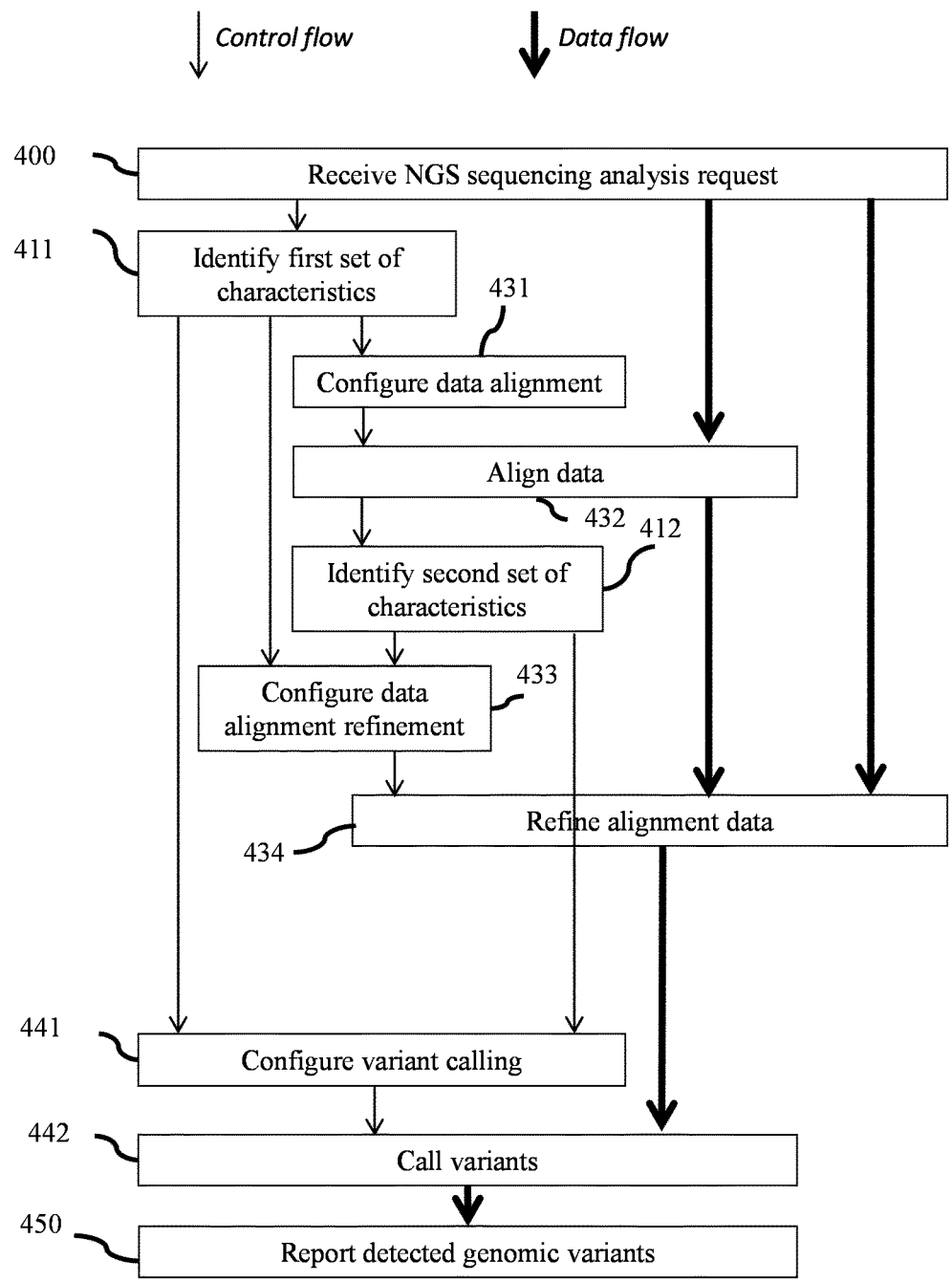
FIG. 4 shows the flowchart of a next generation sequencing genomic analysis workflow according another possible embodiment of the disclosure.

FIG. 4 shows accordingly a workflow for some possible further embodiments of the proposed genomic analysis method, comprising:
  receiving 400 a next generation sequencing analysis request;
  identifying 411 a first set of characteristics associated with the next generation sequencing analysis request, the first set of characteristics comprising at least a target enrichment technology identifier, a sequencing technology identifier, and a gene context identifier;
  configuring 431 a data alignment module 121 to align the input sequencing data in accordance with at least one characteristic of the first set of characteristics;
  aligning 432, with the configured data alignment module 121, the input sequencing data to a genomic sequence, and reporting the alignment data into a raw alignment data file;
  identifying 412 a second set of characteristics associated with the alignment data from the raw alignment data file, the second set of characteristics comprising at least a data alignment pattern identifier;
  configuring 433 a data alignment module 121 to refine at least one subset of the input sequencing data in accordance with at least one characteristic of the first set of characteristics and at least one characteristic of the second set of characteristics;
  refining 434 with the configured data alignment module 121, the subset of the input raw alignment data to produce a refined alignment data file;
  configuring 441 a variant calling module 122 to identify variants associated with the refined alignment data in accordance with at least one characteristic of the first set of characteristics and one characteristic of the second set of characteristics;

identifying 442 genomic variants, with the configured variant calling module 122, in the refined alignment data;

reporting 450 detected genomic variants.

In a possible embodiment, the configured data alignment module 121 executes a re-alignment step 434 directly on the raw alignment data file. In another possible embodiment, the configured data alignment module 121 first extracts a subset of the raw alignment data file, executes a re-alignment step 434 on this subset, and merges the resulting re-alignment data file with the raw alignment data file to produce the refined alignment data file. Other embodiments of the data alignment refinement step 434 are also possible.

In some further embodiments of the present disclosure, the genomic data analyzer 120 may further automatically configure the variant calling module 122 in accordance with the results of the genomic context refinement re-alignment, in particular in the presence of homopolymers and/or complex genomic patterns, for instance with multiple repeats, that are specific to the gene context and may induce further biases in conventional variant calling algorithms. These genomic patterns may be first identified after raw alignment, as part of the second set of characteristics, and may be further confirmed or refined after refined alignment, as a third set of characteristics. The variant calling module 122 may accordingly be configured to apply different variant calling algorithms to different subsets of the refined alignment data, to output a more relevant genomic variant report with increased sensitivity and specificity for variant detection.

Figure 5:
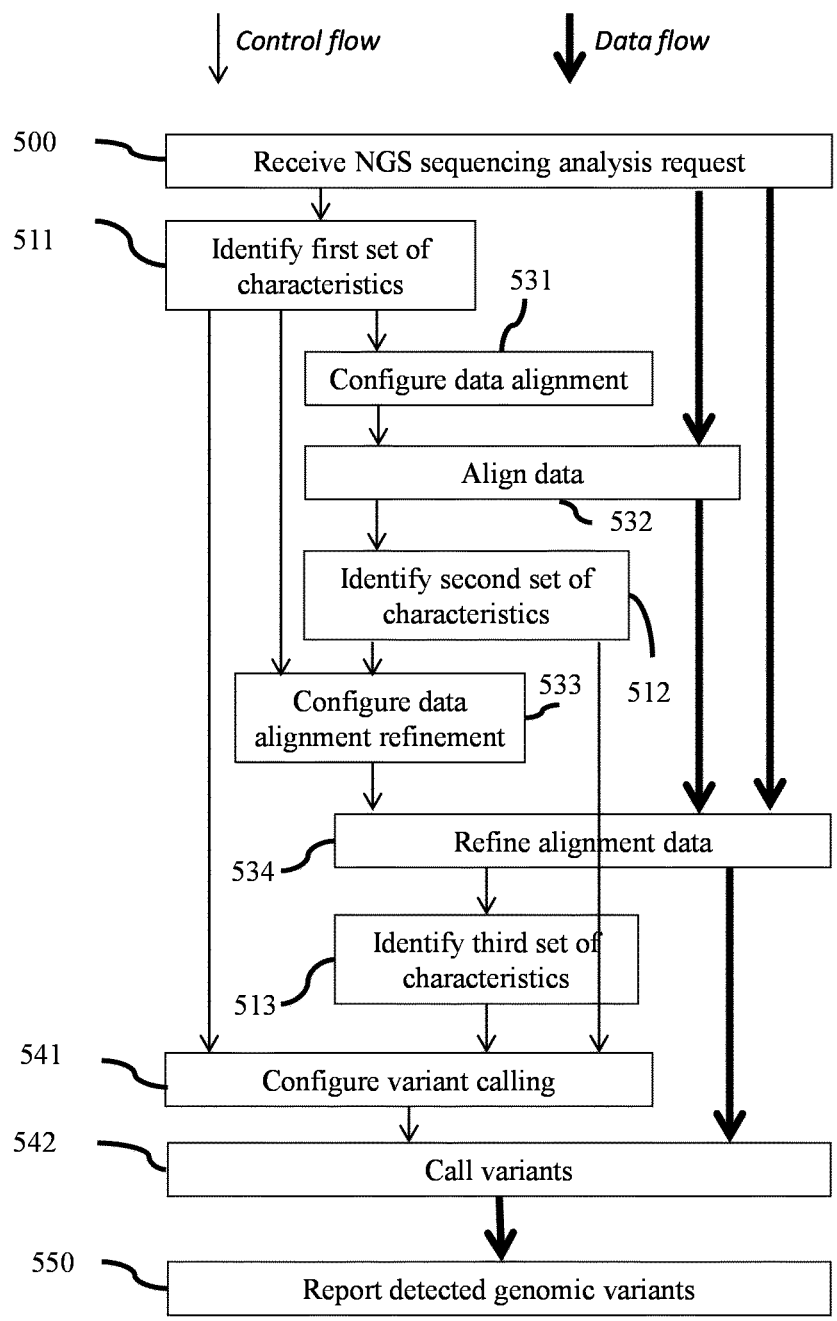
FIG. 5 shows the flowchart of a next generation sequencing genomic analysis workflow according a further possible embodiment of the disclosure.

FIG. 5 shows accordingly a possible further embodiment of the proposed genomic analysis workflow for the genomic data analyzer 120, comprising:

receiving 500 a next generation sequencing analysis request;

identifying 511 a first set of characteristics associated with the next generation sequencing analysis request, the first set of characteristics comprising at least a target enrichment technology identifier, a sequencing technology identifier, and a genomic context identifier;

configuring 531 a data alignment module 121 to align the input sequencing data in accordance with at least one characteristic of the first set of characteristics;

aligning 532, with the configured data alignment module 121, the input sequencing data to a genomic sequence, and reporting the alignment data into a raw alignment data file;

identifying 512 a second set of characteristics associated with the alignment data from the raw alignment data file, the second set of characteristics comprising at least a data alignment pattern identifier;

configuring 533 the data alignment module 121 to refine at least one subset of the input sequencing data in accordance with at least one characteristic of the first set of characteristics and at least one characteristic of the second set of characteristics;

refining 534, with the configured data alignment module 121, the subset of the input raw alignment data to produce a refined alignment data file;

identifying 513 a third set of characteristics associated with the alignment data from the refined alignment data file, the third set of characteristics comprising at least a genomic context identifier;

configuring 541 a variant calling module 122 to identify variants associated with the refined alignment data in accordance with at least one characteristic of the first set of characteristics, at least one characteristic of the second set of characteristics, and at least one characteristic of the third set of characteristics;

identifying 542 genomic variants, with the configured variant calling module 122, in the refined alignment data;

reporting 550 detected genomic variants.

In certain genomic contexts, accurate variant calling is challenged by the combination of insufficient coverage of reads due to the target enrichment or the sequencing technology as identified in the first set of characteristics with alignment failures or ambiguities in subsets of the sequencing data corresponding to challenging gene contexts such as homopolymers, pseudogenes, short tandem repeat polymorphic sites or variable number of tandem repeat sites, and other genomic sequence patterns as identified after initial raw alignment as part the second set of characteristics, or after re-alignment as part of the third set of characteristics. As known to those skilled in the art, the reliability of variant calling may be improved by employing different algorithms, and it is possible to analyze the results of those algorithms to determine if they are applicable or if they need to be refined, or replaced by another algorithm. For instance, whether a given variant shares the same allele with the other variant is not typically inferred at the variant calling step as most of the variant calling algorithms infer each variant independently. Also, the estimation of the variant fraction maybe biased in different enrichment technology, especially for large indels. In a possible further embodiment, the genomic data analyzer 120 may thus identify a fourth set of characteristics after initial variant calling 542, such as a variant calling refinement identifier. The genomic data analyzer 120 may accordingly configure the variant calling module 122 to operate a different algorithm on the initial variant calling 542 data results, for instance to re-estimate the variant fraction or to more accurately determine the phasing information for each variant.

Figure 6:
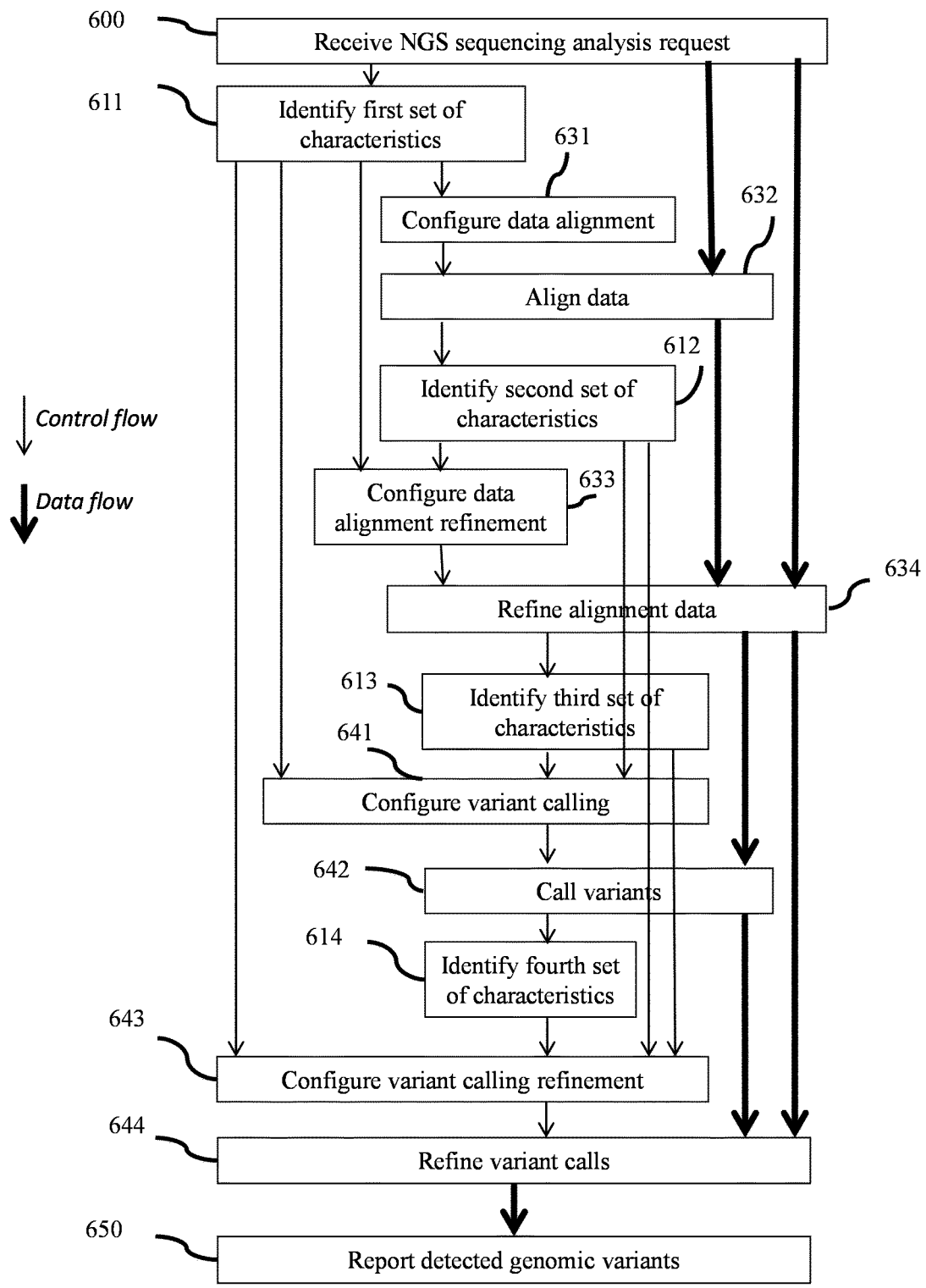
FIG. 6 shows the flowchart of a next generation sequencing genomic analysis workflow according a further possible embodiment of the disclosure.

FIG. 6 shows accordingly a possible further embodiment of the proposed genomic analysis workflow for the genomic data analyzer 120, comprising:

receiving 600 a next generation sequencing analysis request;

identifying 611 a first set of characteristics associated with the next generation sequencing analysis request, the first set of characteristics comprising at least a target enrichment technology identifier, a sequencing technology identifier, and a genomic context identifier;

configuring 631 a data alignment module 121 to align the input sequencing data in accordance with at least one characteristic of the first set of characteristics;

aligning 632, with the configured data alignment module 121, the input sequencing data to a genomic sequence, and reporting the alignment data into a raw alignment data file;

identifying 612 a second set of characteristics associated with the alignment data from the raw alignment data file, the second set of characteristics comprising at least a data alignment pattern identifier;

configuring 633 the data alignment module 121 to refine at least one subset of the input sequencing data in accordance with at least one characteristic of the first set of characteristics and at least one characteristic of the second set of characteristics;

refining 634, with the configured data alignment module 121, the subset of the input sequencing data to produce a refined alignment data file;

identifying 613 a third set of characteristics associated with the re-alignment data from the refined alignment data file, the third set of characteristics comprising at least a genomic context identifier;

configuring 641 a variant calling module 122 to identify variants associated with the refined alignment data in accordance with at least one characteristic of the first set of characteristics, at least one characteristic of the second set of characteristics, and at least one characteristic of the third set of characteristics;

identifying 642 a first set of genomic variants, with the configured variant calling module 122, in the refined alignment data;

identifying 614 a fourth set of characteristics associated with the detected genomic variants, the fourth set of characteristics comprising at least a variant calling refinement identifier;

configuring 643 the variant calling module 122 to identify variants associated with the refined alignment data in accordance with at least one characteristic of the first set of characteristics, at least one characteristic of the second set of characteristics, at least one characteristic of the third set of characteristics and at least one characteristic of the fourth set of characteristics;

identifying 644 refined genomic variants, with the configured variant calling module 122, in the refined alignment data and the detected genomic variants, to produce a refined set of genomic variants;

reporting 650 the refined set of genomic variants.

Exemplary Embodiments

Exemplary embodiments of the proposed genomic analysis method will now be described in more detail for a genomic data analyzer system 120, as illustrated on FIG. 2, adapted to run four different genomic analyses in different possible workflow configurations, as represented by FIG. 6.

The genomic data analyzer 120 serves two sourcing laboratories, Lab #1 and Lab #2. Lab #1 operates an Illumina sequencer MiSeq® with Reagent Kit v3, which has a sequencing capacity of 15 Gb@2×300 bp for up to 25 millions total reads, and different DNA enrichment assays such as:

Kit #k1: The Integrated DNA Technologies xGen® AML Cancer Panel v1.0. This panel comprises more than 10000 xGen Lockdown® probes for targeted enrichment of more than 260 genes to detect human genome mutations associated with Acute Myeloid Leukemia (AML).

Kit #k2: The Multiplicom CFTR MASTR™ Dx targeting the CFTR gene associated with mutations frequently causing cystic fibrosis in individuals from European descent. This technology uses 48 amplicons of 300 bp to 450 bp and primer probes of 20 bp to 30 bp, and is typically operated with pair-ended read length of 250 bp pair-ended reads.

Kit #k3: The Illumina® Trusight® Myeloid Panel targeting 54 genes associated with mutations frequently causing myeloid malignancies. This technology uses amplicons of 225 bp to 275 bp and primer probes of 22 bp to 30 bp, and is typically operated with pair-ended read length of 150 bp pair-ended reads.

Lab #2 is associated with an Ion PGM™ sequencing system with the 318™ sequencer chip technology and operates:

the Multiplicom BRCA MASTR™ Dx assay to detect mutations from 2 genes associated with certain hereditary forms of breast and ovarian cancers. This assay uses 93 amplicons of 289 bp to 430 bp, and is typically operated with of 250 bp to 300 bp pair-ended reads or possibly with unidirectional reads of 200 bp for Ion Torrent PGM™ sequencing, yet subject to an additional short fragment generation step (also known as shearing) in the library preparation in the latter case.

The laboratory information database thus lists the following combinations of sequencer, target enrichment technology and genomic context identifiers information for Lab #1 and Lab #2 respectively:

TABLE 1

Examplary extract of laboratory information listing.

| Lab | Sequencer | Target enrichment technology | Target gene |
|---|---|---|---|
| #1 | Illumina ® MiSeq ® Reagent Kit v3 | Integrated DNA Technologies xGen ® AML Cancer Panel v1.0 | ADCY5 |
| #1 | Illumina ® MiSeq ® Reagent Kit v3 | Integrated DNA Technologies xGen ® AML Cancer Panel v1.0 | ANK2 |
| #1 | Illumina ® MiSeq ® Reagent Kit v3 | Integrated DNA Technologies xGen ® AML Cancer Panel v1.0 | APOB |
| #1 | Illumina ® MiSeq ® Reagent Kit v3 | Integrated DNA Technologies xGen ® AML Cancer Panel v1.0 | SHROOM2 |
| #1 | Illumina ® MiSeq ® Reagent Kit v3 | Integrated DNA Technologies xGen ® AML Cancer Panel v1.0 | ATP2B3 |
| #1 | Illumina ® MiSeq ® Reagent Kit v3 | Integrated DNA Technologies xGen ® AML Cancer Panel v1.0 | DST |
| #1 | Illumina ® MiSeq ® Reagent Kit v3 | Integrated DNA Technologies xGen ® AML Cancer Panel v1.0 | C5 |
| #1 | Illumina ® MiSeq ® Reagent Kit v3 | Integrated DNA Technologies xGen ® AML Cancer Panel v1.0 | CACNA1B |
| #1 | Illumina ® MiSeq ® Reagent Kit v3 | Integrated DNA Technologies xGen ® AML Cancer Panel v1.0 | CACNA1E |
| #1 | Illumina ® MiSeq ® Reagent Kit v3 | Integrated DNA Technologies xGen ® AML Cancer Panel v1.0 | CALR |
| #1 | Illumina ® MiSeq ® Reagent Kit v3 | Integrated DNA Technologies xGen ® AML Cancer Panel v1.0 | RUNX1 |
| #1 | Illumina ® MiSeq ® Reagent Kit v3 | Integrated DNA Technologies xGen ® AML Cancer Panel v1.0 | RUNX1T1 |
| #1 | Illumina ® MiSeq ® Reagent Kit v3 | Integrated DNA Technologies xGen ® AML Cancer Panel v1.0 | CBFB |
| #1 | Illumina ® MiSeq ® Reagent Kit v3 | Integrated DNA Technologies xGen ® AML Cancer Panel v1.0 | CBL |
| #1 | Illumina ® MiSeq ® Reagent Kit v3 | Integrated DNA Technologies xGen ® AML Cancer Panel v1.0 | SCARB1 |
| #1 | Illumina ® MiSeq ® Reagent Kit v3 | Integrated DNA Technologies xGen ® AML Cancer Panel v1.0 | CD74 |
| #1 | Illumina ® MiSeq ® Reagent Kit v3 | Integrated DNA Technologies xGen ® AML Cancer Panel v1.0 | LRBA |
| #1 | Illumina ® MiSeq ® Reagent Kit v3 | Integrated DNA Technologies xGen ® AML Cancer Panel v1.0 | CEBPA |
| #1 | Illumina ® MiSeq ® Reagent Kit v3 | Integrated DNA Technologies xGen ® AML Cancer Panel v1.0 | CHD4 |
| #1 | Illumina ® MiSeq ® Reagent Kit v3 | Integrated DNA Technologies xGen ® AML Cancer Panel v1.0 | COL12A1 |
| #1 | Illumina ® MiSeq ® Reagent Kit v3 | Integrated DNA Technologies xGen ® AML Cancer Panel v1.0 | VCAN |
| #1 | Illumina ® MiSeq ® Reagent Kit v3 | Integrated DNA Technologies xGen ® AML Cancer Panel v1.0 | DDX11 |
| #1 | Illumina ® MiSeq ® Reagent Kit v3 | Integrated DNA Technologies xGen ® AML Cancer Panel v1.0 | DNAH5 |
| #1 | Illumina ® MiSeq ® Reagent Kit v3 | Integrated DNA Technologies xGen ® AML Cancer Panel v1.0 | DNAH9 |
| #1 | Illumina ® MiSeq ® Reagent Kit v3 | Integrated DNA Technologies xGen ® AML Cancer Panel v1.0 | DNMT3A |
| #1 | Illumina ® MiSeq ® Reagent Kit v3 | Integrated DNA Technologies xGen ® AML Cancer Panel v1.0 | DNMT3B |

TABLE 1-continued

Examplary extract of laboratory information listing.

| Lab | Sequencer | Target enrichment technology | Target gene |
|---|---|---|---|
| #1 | Illumina ® MiSeq ® Reagent Kit v3 | Integrated DNA Technologies xGen ® AML Cancer Panel v1.0 | DOCK2 |
| #1 | Illumina ® MiSeq ® Reagent Kit v3 | Integrated DNA Technologies xGen ® AML Cancer Panel v1.0 | DRD2 |
| #1 | Illumina ® MiSeq ® Reagent Kit v3 | Integrated DNA Technologies xGen ® AML Cancer Panel v1.0 | DSCAM |
| #1 | Illumina ® MiSeq ® Reagent Kit v3 | Integrated DNA Technologies xGen ® AML Cancer Panel v1.0 | GPR183 |
| #1 | Illumina ® MiSeq ® Reagent Kit v3 | Integrated DNA Technologies xGen ® AML Cancer Panel v1.0 | CELSR3 |
| #1 | Illumina ® MiSeq ® Reagent Kit v3 | Integrated DNA Technologies xGen ® AML Cancer Panel v1.0 | MEGF8 |
| #1 | Illumina ® MiSeq ® Reagent Kit v3 | Integrated DNA Technologies xGen ® AML Cancer Panel v1.0 | EGFR |
| #1 | Illumina ® MiSeq ® Reagent Kit v3 | Integrated DNA Technologies xGen ® AML Cancer Panel v1.0 | ETV6 |
| #1 | Illumina ® MiSeq ® Reagent Kit v3 | Integrated DNA Technologies xGen ® AML Cancer Panel v1.0 | EZH2 |
| #1 | Illumina ® MiSeq ® Reagent Kit v3 | Integrated DNA Technologies xGen ® AML Cancer Panel v1.0 | FLG |
| #1 | Illumina ® MiSeq ® Reagent Kit v3 | Integrated DNA Technologies xGen ® AML Cancer Panel v1.0 | FLT1 |
| #1 | Illumina ® MiSeq ® Reagent Kit v3 | Integrated DNA Technologies xGen ® AML Cancer Panel v1.0 | FLT3 |
| #1 | Illumina ® MiSeq ® Reagent Kit v3 | Integrated DNA Technologies xGen ® AML Cancer Panel v1.0 | GAS6 |
| #1 | Illumina ® MiSeq ® Reagent Kit v3 | Integrated DNA Technologies xGen ® AML Cancer Panel v1.0 | GATA2 |
| #1 | Illumina ® MiSeq ® Reagent Kit v3 | Integrated DNA Technologies xGen ® AML Cancer Panel v1.0 | GJB3 |
| #1 | Illumina ® MiSeq ® Reagent Kit v3 | Integrated DNA Technologies xGen ® AML Cancer Panel v1.0 | GRID1 |
| #1 | Illumina ® MiSeq ® Reagent Kit v3 | Integrated DNA Technologies xGen ® AML Cancer Panel v1.0 | GRIK2 |
| #1 | Illumina ® MiSeq ® Reagent Kit v3 | Integrated DNA Technologies xGen ® AML Cancer Panel v1.0 | GRIK4 |
| #1 | Illumina ® MiSeq ® Reagent Kit v3 | Integrated DNA Technologies xGen ® AML Cancer Panel v1.0 | GRM3 |
| #1 | Illumina ® MiSeq ® Reagent Kit v3 | Integrated DNA Technologies xGen ® AML Cancer Panel v1.0 | GRM8 |
| #1 | Illumina ® MiSeq ® Reagent Kit v3 | Integrated DNA Technologies xGen ® AML Cancer Panel v1.0 | HIVEP1 |
| #1 | Illumina ® MiSeq ® Reagent Kit v3 | Integrated DNA Technologies xGen ® AML Cancer Panel v1.0 | HNRNPK |
| #1 | Illumina ® MiSeq ® Reagent Kit v3 | Integrated DNA Technologies xGen ® AML Cancer Panel v1.0 | TNC |
| #1 | Illumina ® MiSeq ® Reagent Kit v3 | Integrated DNA Technologies xGen ® AML Cancer Panel v1.0 | IDH1 |
| #1 | Illumina ® MiSeq ® Reagent Kit v3 | Integrated DNA Technologies xGen ® AML Cancer Panel v1.0 | IDH2 |
| #1 | Illumina ® MiSeq ® Reagent Kit v3 | Integrated DNA Technologies xGen ® AML Cancer Panel v1.0 | ITPR3 |
| #1 | Illumina ® MiSeq ® Reagent Kit v3 | Integrated DNA Technologies xGen ® AML Cancer Panel v1.0 | JAK1 |
| #1 | Illumina ® MiSeq ® Reagent Kit v3 | Integrated DNA Technologies xGen ® AML Cancer Panel v1.0 | JAK2 |
| #1 | Illumina ® MiSeq ® Reagent Kit v3 | Integrated DNA Technologies xGen ® AML Cancer Panel v1.0 | JAK3 |
| #1 | Illumina ® MiSeq ® Reagent Kit v3 | Integrated DNA Technologies xGen ® AML Cancer Panel v1.0 | KCNA4 |
| #1 | Illumina ® MiSeq ® Reagent Kit v3 | Integrated DNA Technologies xGen ® AML Cancer Panel v1.0 | KCNH2 |
| #1 | Illumina ® MiSeq ® Reagent Kit v3 | Integrated DNA Technologies xGen ® AML Cancer Panel v1.0 | KCNQ2 |
| #1 | Illumina ® MiSeq ® Reagent Kit v3 | Integrated DNA Technologies xGen ® AML Cancer Panel v1.0 | KDR |
| #1 | Illumina ® MiSeq ® Reagent Kit v3 | Integrated DNA Technologies xGen ® AML Cancer Panel v1.0 | KIT |
| #1 | Illumina ® MiSeq ® Reagent Kit v3 | Integrated DNA Technologies xGen ® AML Cancer Panel v1.0 | KRAS |
| #1 | Illumina ® MiSeq ® Reagent Kit v3 | Integrated DNA Technologies xGen ® AML Cancer Panel v1.0 | KRT19 |
| #1 | Illumina ® MiSeq ® Reagent Kit v3 | Integrated DNA Technologies xGen ® AML Cancer Panel v1.0 | MAP1B |
| #1 | Illumina ® MiSeq ® Reagent Kit v3 | Integrated DNA Technologies xGen ® AML Cancer Panel v1.0 | MAP2 |
| #1 | Illumina ® MiSeq ® Reagent Kit v3 | Integrated DNA Technologies xGen ® AML Cancer Panel v1.0 | ADAM11 |
| #1 | Illumina ® MiSeq ® Reagent Kit v3 | Integrated DNA Technologies xGen ® AML Cancer Panel v1.0 | MEFV |
| #1 | Illumina ® MiSeq ® Reagent Kit v3 | Integrated DNA Technologies xGen ® AML Cancer Panel v1.0 | MYC |
| #1 | Illumina ® MiSeq ® Reagent Kit v3 | Integrated DNA Technologies xGen ® AML Cancer Panel v1.0 | MYH4 |
| #1 | Illumina ® MiSeq ® Reagent Kit v3 | Integrated DNA Technologies xGen ® AML Cancer Panel v1.0 | MYO5B |
| #1 | Illumina ® MiSeq ® Reagent Kit v3 | Integrated DNA Technologies xGen ® AML Cancer Panel v1.0 | MYOC |
| #1 | Illumina ® MiSeq ® Reagent Kit v3 | Integrated DNA Technologies xGen ® AML Cancer Panel v1.0 | NF1 |
| #1 | Illumina ® MiSeq ® Reagent Kit v3 | Integrated DNA Technologies xGen ® AML Cancer Panel v1.0 | NPM1 |
| #1 | Illumina ® MiSeq ® Reagent Kit v3 | Integrated DNA Technologies xGen ® AML Cancer Panel v1.0 | NRAS |
| #1 | Illumina ® MiSeq ® Reagent Kit v3 | Integrated DNA Technologies xGen ® AML Cancer Panel v1.0 | NTRK3 |
| #1 | Illumina ® MiSeq ® Reagent Kit v3 | Integrated DNA Technologies xGen ® AML Cancer Panel v1.0 | DDR2 |
| #1 | Illumina ® MiSeq ® Reagent Kit v3 | Integrated DNA Technologies xGen ® AML Cancer Panel v1.0 | P2RY2 |
| #1 | Illumina ® MiSeq ® Reagent Kit v3 | Integrated DNA Technologies xGen ® AML Cancer Panel v1.0 | PKHD1 |
| #1 | Illumina ® MiSeq ® Reagent Kit v3 | Integrated DNA Technologies xGen ® AML Cancer Panel v1.0 | PPP1R3A |
| #1 | Illumina ® MiSeq ® Reagent Kit v3 | Integrated DNA Technologies xGen ® AML Cancer Panel v1.0 | PTCH1 |
| #1 | Illumina ® MiSeq ® Reagent Kit v3 | Integrated DNA Technologies xGen ® AML Cancer Panel v1.0 | PTPN11 |
| #1 | Illumina ® MiSeq ® Reagent Kit v3 | Integrated DNA Technologies xGen ® AML Cancer Panel v1.0 | PTPRN |
| #1 | Illumina ® MiSeq ® Reagent Kit v3 | Integrated DNA Technologies xGen ® AML Cancer Panel v1.0 | RAD21 |
| #1 | Illumina ® MiSeq ® Reagent Kit v3 | Integrated DNA Technologies xGen ® AML Cancer Panel v1.0 | RBBP4 |
| #1 | Illumina ® MiSeq ® Reagent Kit v3 | Integrated DNA Technologies xGen ® AML Cancer Panel v1.0 | RFC3 |
| #1 | Illumina ® MiSeq ® Reagent Kit v3 | Integrated DNA Technologies xGen ® AML Cancer Panel v1.0 | RYR1 |
| #1 | Illumina ® MiSeq ® Reagent Kit v3 | Integrated DNA Technologies xGen ® AML Cancer Panel v1.0 | RYR3 |
| #1 | Illumina ® MiSeq ® Reagent Kit v3 | Integrated DNA Technologies xGen ® AML Cancer Panel v1.0 | SCN1A |
| #1 | Illumina ® MiSeq ® Reagent Kit v3 | Integrated DNA Technologies xGen ® AML Cancer Panel v1.0 | SRSF2 |
| #1 | Illumina ® MiSeq ® Reagent Kit v3 | Integrated DNA Technologies xGen ® AML Cancer Panel v1.0 | TRA2B |
| #1 | Illumina ® MiSeq ® Reagent Kit v3 | Integrated DNA Technologies xGen ® AML Cancer Panel v1.0 | SHC1 |
| #1 | Illumina ® MiSeq ® Reagent Kit v3 | Integrated DNA Technologies xGen ® AML Cancer Panel v1.0 | SI |
| #1 | Illumina ® MiSeq ® Reagent Kit v3 | Integrated DNA Technologies xGen ® AML Cancer Panel v1.0 | SLC12A3 |
| #1 | Illumina ® MiSeq ® Reagent Kit v3 | Integrated DNA Technologies xGen ® AML Cancer Panel v1.0 | STRN |
| #1 | Illumina ® MiSeq ® Reagent Kit v3 | Integrated DNA Technologies xGen ® AML Cancer Panel v1.0 | NR2E1 |
| #1 | Illumina ® MiSeq ® Reagent Kit v3 | Integrated DNA Technologies xGen ® AML Cancer Panel v1.0 | TP53 |
| #1 | Illumina ® MiSeq ® Reagent Kit v3 | Integrated DNA Technologies xGen ® AML Cancer Panel v1.0 | TUBA3C |
| #1 | Illumina ® MiSeq ® Reagent Kit v3 | Integrated DNA Technologies xGen ® AML Cancer Panel v1.0 | TYK2 |
| #1 | Illumina ® MiSeq ® Reagent Kit v3 | Integrated DNA Technologies xGen ® AML Cancer Panel v1.0 | U2AF1 |
| #1 | Illumina ® MiSeq ® Reagent Kit v3 | Integrated DNA Technologies xGen ® AML Cancer Panel v1.0 | KDM6A |
| #1 | Illumina ® MiSeq ® Reagent Kit v3 | Integrated DNA Technologies xGen ® AML Cancer Panel v1.0 | WT1 |
| #1 | Illumina ® MiSeq ® Reagent Kit v3 | Integrated DNA Technologies xGen ® AML Cancer Panel v1.0 | USP9X |
| #1 | Illumina ® MiSeq ® Reagent Kit v3 | Integrated DNA Technologies xGen ® AML Cancer Panel v1.0 | SMC1A |

TABLE 1-continued

Examplary extract of laboratory information listing.

| Lab | Sequencer | Target enrichment technology | Target gene |
|---|---|---|---|
| #1 | Illumina ® MiSeq ® Reagent Kit v3 | Integrated DNA Technologies xGen ® AML Cancer Panel v1.0 | DYSF |
| #1 | Illumina ® MiSeq ® Reagent Kit v3 | Integrated DNA Technologies xGen ® AML Cancer Panel v1.0 | CUL1 |
| #1 | Illumina ® MiSeq ® Reagent Kit v3 | Integrated DNA Technologies xGen ® AML Cancer Panel v1.0 | STC2 |
| #1 | Illumina ® MiSeq ® Reagent Kit v3 | Integrated DNA Technologies xGen ® AML Cancer Panel v1.0 | CADPS |
| #1 | Illumina ® MiSeq ® Reagent Kit v3 | Integrated DNA Technologies xGen ® AML Cancer Panel v1.0 | EED |
| #1 | Illumina ® MiSeq ® Reagent Kit v3 | Integrated DNA Technologies xGen ® AML Cancer Panel v1.0 | SYNGAP1 |
| #1 | Illumina ® MiSeq ® Reagent Kit v3 | Integrated DNA Technologies xGen ® AML Cancer Panel v1.0 | FCGBP |
| #1 | Illumina ® MiSeq ® Reagent Kit v3 | Integrated DNA Technologies xGen ® AML Cancer Panel v1.0 | PRPF4B |
| #1 | Illumina ® MiSeq ® Reagent Kit v3 | Integrated DNA Technologies xGen ® AML Cancer Panel v1.0 | CACNA1G |
| #1 | Illumina ® MiSeq ® Reagent Kit v3 | Integrated DNA Technologies xGen ® AML Cancer Panel v1.0 | BSN |
| #1 | Illumina ® MiSeq ® Reagent Kit v3 | Integrated DNA Technologies xGen ® AML Cancer Panel v1.0 | TOP3B |
| #1 | Illumina ® MiSeq ® Reagent Kit v3 | Integrated DNA Technologies xGen ® AML Cancer Panel v1.0 | PKD2L1 |
| #1 | Illumina ® MiSeq ® Reagent Kit v3 | Integrated DNA Technologies xGen ® AML Cancer Panel v1.0 | SMC3 |
| #1 | Illumina ® MiSeq ® Reagent Kit v3 | Integrated DNA Technologies xGen ® AML Cancer Panel v1.0 | DCLK1 |
| #1 | Illumina ® MiSeq ® Reagent Kit v3 | Integrated DNA Technologies xGen ® AML Cancer Panel v1.0 | MTA2 |
| #1 | Illumina ® MiSeq ® Reagent Kit v3 | Integrated DNA Technologies xGen ® AML Cancer Panel v1.0 | NRXN3 |
| #1 | Illumina ® MiSeq ® Reagent Kit v3 | Integrated DNA Technologies xGen ® AML Cancer Panel v1.0 | ABCG2 |
| #1 | Illumina ® MiSeq ® Reagent Kit v3 | Integrated DNA Technologies xGen ® AML Cancer Panel v1.0 | CROCC |
| #1 | Illumina ® MiSeq ® Reagent Kit v3 | Integrated DNA Technologies xGen ® AML Cancer Panel v1.0 | MAGI2 |
| #1 | Illumina ® MiSeq ® Reagent Kit v3 | Integrated DNA Technologies xGen ® AML Cancer Panel v1.0 | THRAP3 |
| #1 | Illumina ® MiSeq ® Reagent Kit v3 | Integrated DNA Technologies xGen ® AML Cancer Panel v1.0 | MED12 |
| #1 | Illumina ® MiSeq ® Reagent Kit v3 | Integrated DNA Technologies xGen ® AML Cancer Panel v1.0 | ZBTB33 |
| #1 | Illumina ® MiSeq ® Reagent Kit v3 | Integrated DNA Technologies xGen ® AML Cancer Panel v1.0 | EDIL3 |
| #1 | Illumina ® MiSeq ® Reagent Kit v3 | Integrated DNA Technologies xGen ® AML Cancer Panel v1.0 | SPEG |
| #1 | Illumina ® MiSeq ® Reagent Kit v3 | Integrated DNA Technologies xGen ® AML Cancer Panel v1.0 | SEMA3A |
| #1 | Illumina ® MiSeq ® Reagent Kit v3 | Integrated DNA Technologies xGen ® AML Cancer Panel v1.0 | SCML2 |
| #1 | Illumina ® MiSeq ® Reagent Kit v3 | Integrated DNA Technologies xGen ® AML Cancer Panel v1.0 | DLC1 |
| #1 | Illumina ® MiSeq ® Reagent Kit v3 | Integrated DNA Technologies xGen ® AML Cancer Panel v1.0 | PRPF8 |
| #1 | Illumina ® MiSeq ® Reagent Kit v3 | Integrated DNA Technologies xGen ® AML Cancer Panel v1.0 | STAG2 |
| #1 | Illumina ® MiSeq ® Reagent Kit v3 | Integrated DNA Technologies xGen ® AML Cancer Panel v1.0 | PTPRT |
| #1 | Illumina ® MiSeq ® Reagent Kit v3 | Integrated DNA Technologies xGen ® AML Cancer Panel v1.0 | AKAP13 |
| #1 | Illumina ® MiSeq ® Reagent Kit v3 | Integrated DNA Technologies xGen ® AML Cancer Panel v1.0 | SCAF8 |
| #1 | Illumina ® MiSeq ® Reagent Kit v3 | Integrated DNA Technologies xGen ® AML Cancer Panel v1.0 | DIS3 |
| #1 | Illumina ® MiSeq ® Reagent Kit v3 | Integrated DNA Technologies xGen ® AML Cancer Panel v1.0 | RIMS1 |
| #1 | Illumina ® MiSeq ® Reagent Kit v3 | Integrated DNA Technologies xGen ® AML Cancer Panel v1.0 | SPEN |
| #1 | Illumina ® MiSeq ® Reagent Kit v3 | Integrated DNA Technologies xGen ® AML Cancer Panel v1.0 | SMG1 |
| #1 | Illumina ® MiSeq ® Reagent Kit v3 | Integrated DNA Technologies xGen ® AML Cancer Panel v1.0 | HECW1 |
| #1 | Illumina ® MiSeq ® Reagent Kit v3 | Integrated DNA Technologies xGen ® AML Cancer Panel v1.0 | ATP10B |
| #1 | Illumina ® MiSeq ® Reagent Kit v3 | Integrated DNA Technologies xGen ® AML Cancer Panel v1.0 | PSME4 |
| #1 | Illumina ® MiSeq ® Reagent Kit v3 | Integrated DNA Technologies xGen ® AML Cancer Panel v1.0 | MTUS2 |
| #1 | Illumina ® MiSeq ® Reagent Kit v3 | Integrated DNA Technologies xGen ® AML Cancer Panel v1.0 | SF3B1 |
| #1 | Illumina ® MiSeq ® Reagent Kit v3 | Integrated DNA Technologies xGen ® AML Cancer Panel v1.0 | KIAA0240 |
| #1 | Illumina ® MiSeq ® Reagent Kit v3 | Integrated DNA Technologies xGen ® AML Cancer Panel v1.0 | SUZ12 |
| #1 | Illumina ® MiSeq ® Reagent Kit v3 | Integrated DNA Technologies xGen ® AML Cancer Panel v1.0 | FLRT2 |
| #1 | Illumina ® MiSeq ® Reagent Kit v3 | Integrated DNA Technologies xGen ® AML Cancer Panel v1.0 | FKBP8 |
| #1 | Illumina ® MiSeq ® Reagent Kit v3 | Integrated DNA Technologies xGen ® AML Cancer Panel v1.0 | SETBP1 |
| #1 | Illumina ® MiSeq ® Reagent Kit v3 | Integrated DNA Technologies xGen ® AML Cancer Panel v1.0 | GIGYF2 |
| #1 | Illumina ® MiSeq ® Reagent Kit v3 | Integrated DNA Technologies xGen ® AML Cancer Panel v1.0 | LRIT1 |
| #1 | Illumina ® MiSeq ® Reagent Kit v3 | Integrated DNA Technologies xGen ® AML Cancer Panel v1.0 | DNAI1 |
| #1 | Illumina ® MiSeq ® Reagent Kit v3 | Integrated DNA Technologies xGen ® AML Cancer Panel v1.0 | FOXP1 |
| #1 | Illumina ® MiSeq ® Reagent Kit v3 | Integrated DNA Technologies xGen ® AML Cancer Panel v1.0 | C10orf28 |
| #1 | Illumina ® MiSeq ® Reagent Kit v3 | Integrated DNA Technologies xGen ® AML Cancer Panel v1.0 | CECR2 |
| #1 | Illumina ® MiSeq ® Reagent Kit v3 | Integrated DNA Technologies xGen ® AML Cancer Panel v1.0 | PCDHB1 |
| #1 | Illumina ® MiSeq ® Reagent Kit v3 | Integrated DNA Technologies xGen ® AML Cancer Panel v1.0 | COL5A3 |
| #1 | Illumina ® MiSeq ® Reagent Kit v3 | Integrated DNA Technologies xGen ® AML Cancer Panel v1.0 | PLCE1 |
| #1 | Illumina ® MiSeq ® Reagent Kit v3 | Integrated DNA Technologies xGen ® AML Cancer Panel v1.0 | WAC |
| #1 | Illumina ® MiSeq ® Reagent Kit v3 | Integrated DNA Technologies xGen ® AML Cancer Panel v1.0 | DDX41 |
| #1 | Illumina ® MiSeq ® Reagent Kit v3 | Integrated DNA Technologies xGen ® AML Cancer Panel v1.0 | KDM3B |
| #1 | Illumina ® MiSeq ® Reagent Kit v3 | Integrated DNA Technologies xGen ® AML Cancer Panel v1.0 | LRP1B |
| #1 | Illumina ® MiSeq ® Reagent Kit v3 | Integrated DNA Technologies xGen ® AML Cancer Panel v1.0 | CNTN5 |
| #1 | Illumina ® MiSeq ® Reagent Kit v3 | Integrated DNA Technologies xGen ® AML Cancer Panel v1.0 | PCDHB18 |
| #1 | Illumina ® MiSeq ® Reagent Kit v3 | Integrated DNA Technologies xGen ® AML Cancer Panel v1.0 | HYDIN |
| #1 | Illumina ® MiSeq ® Reagent Kit v3 | Integrated DNA Technologies xGen ® AML Cancer Panel v1.0 | TET2 |
| #1 | Illumina ® MiSeq ® Reagent Kit v3 | Integrated DNA Technologies xGen ® AML Cancer Panel v1.0 | DCHS2 |
| #1 | Illumina ® MiSeq ® Reagent Kit v3 | Integrated DNA Technologies xGen ® AML Cancer Panel v1.0 | TMEM104 |
| #1 | Illumina ® MiSeq ® Reagent Kit v3 | Integrated DNA Technologies xGen ® AML Cancer Panel v1.0 | BCOR |
| #1 | Illumina ® MiSeq ® Reagent Kit v3 | Integrated DNA Technologies xGen ® AML Cancer Panel v1.0 | PHIP |
| #1 | Illumina ® MiSeq ® Reagent Kit v3 | Integrated DNA Technologies xGen ® AML Cancer Panel v1.0 | ATG16L1 |
| #1 | Illumina ® MiSeq ® Reagent Kit v3 | Integrated DNA Technologies xGen ® AML Cancer Panel v1.0 | C10orf118 |
| #1 | Illumina ® MiSeq ® Reagent Kit v3 | Integrated DNA Technologies xGen ® AML Cancer Panel v1.0 | MTMR8 |
| #1 | Illumina ® MiSeq ® Reagent Kit v3 | Integrated DNA Technologies xGen ® AML Cancer Panel v1.0 | CACNA2D3 |
| #1 | Illumina ® MiSeq ® Reagent Kit v3 | Integrated DNA Technologies xGen ® AML Cancer Panel v1.0 | PCDHA13 |
| #1 | Illumina ® MiSeq ® Reagent Kit v3 | Integrated DNA Technologies xGen ® AML Cancer Panel v1.0 | PCDHA6 |
| #1 | Illumina ® MiSeq ® Reagent Kit v3 | Integrated DNA Technologies xGen ® AML Cancer Panel v1.0 | KCNK13 |
| #1 | Illumina ® MiSeq ® Reagent Kit v3 | Integrated DNA Technologies xGen ® AML Cancer Panel v1.0 | NMUR2 |
| #1 | Illumina ® MiSeq ® Reagent Kit v3 | Integrated DNA Technologies xGen ® AML Cancer Panel v1.0 | VARS2 |

TABLE 1-continued

Examplary extract of laboratory information listing.

| Lab | Sequencer | Target enrichment technology | Target gene |
|---|---|---|---|
| #1 | Illumina ® MiSeq ® Reagent Kit v3 | Integrated DNA Technologies xGen ® AML Cancer Panel v1.0 | FAM40B |
| #1 | Illumina ® MiSeq ® Reagent Kit v3 | Integrated DNA Technologies xGen ® AML Cancer Panel v1.0 | PLEKHH1 |
| #1 | Illumina ® MiSeq ® Reagent Kit v3 | Integrated DNA Technologies xGen ® AML Cancer Panel v1.0 | ALPK3 |
| #1 | Illumina ® MiSeq ® Reagent Kit v3 | Integrated DNA Technologies xGen ® AML Cancer Panel v1.0 | KCNT1 |
| #1 | Illumina ® MiSeq ® Reagent Kit v3 | Integrated DNA Technologies xGen ® AML Cancer Panel v1.0 | ZNF687 |
| #1 | Illumina ® MiSeq ® Reagent Kit v3 | Integrated DNA Technologies xGen ® AML Cancer Panel v1.0 | KIAA1529 |
| #1 | Illumina ® MiSeq ® Reagent Kit v3 | Integrated DNA Technologies xGen ® AML Cancer Panel v1.0 | RNF213 |
| #1 | Illumina ® MiSeq ® Reagent Kit v3 | Integrated DNA Technologies xGen ® AML Cancer Panel v1.0 | NLRC4 |
| #1 | Illumina ® MiSeq ® Reagent Kit v3 | Integrated DNA Technologies xGen ® AML Cancer Panel v1.0 | MLL3 |
| #1 | Illumina ® MiSeq ® Reagent Kit v3 | Integrated DNA Technologies xGen ® AML Cancer Panel v1.0 | LRRC4 |
| #1 | Illumina ® MiSeq ® Reagent Kit v3 | Integrated DNA Technologies xGen ® AML Cancer Panel v1.0 | SEMA4A |
| #1 | Illumina ® MiSeq ® Reagent Kit v3 | Integrated DNA Technologies xGen ® AML Cancer Panel v1.0 | IKZF4 |
| #1 | Illumina ® MiSeq ® Reagent Kit v3 | Integrated DNA Technologies xGen ® AML Cancer Panel v1.0 | CSMD1 |
| #1 | Illumina ® MiSeq ® Reagent Kit v3 | Integrated DNA Technologies xGen ® AML Cancer Panel v1.0 | PRAMEF2 |
| #1 | Illumina ® MiSeq ® Reagent Kit v3 | Integrated DNA Technologies xGen ® AML Cancer Panel v1.0 | FAM65A |
| #1 | Illumina ® MiSeq ® Reagent Kit v3 | Integrated DNA Technologies xGen ® AML Cancer Panel v1.0 | DYNC2H1 |
| #1 | Illumina ® MiSeq ® Reagent Kit v3 | Integrated DNA Technologies xGen ® AML Cancer Panel v1.0 | E2F8 |
| #1 | Illumina ® MiSeq ® Reagent Kit v3 | Integrated DNA Technologies xGen ® AML Cancer Panel v1.0 | TRPM3 |
| #1 | Illumina ® MiSeq ® Reagent Kit v3 | Integrated DNA Technologies xGen ® AML Cancer Panel v1.0 | TET1 |
| #1 | Illumina ® MiSeq ® Reagent Kit v3 | Integrated DNA Technologies xGen ® AML Cancer Panel v1.0 | ABTB1 |
| #1 | Illumina ® MiSeq ® Reagent Kit v3 | Integrated DNA Technologies xGen ® AML Cancer Panel v1.0 | KIAA1683 |
| #1 | Illumina ® MiSeq ® Reagent Kit v3 | Integrated DNA Technologies xGen ® AML Cancer Panel v1.0 | EPPK1 |
| #1 | Illumina ® MiSeq ® Reagent Kit v3 | Integrated DNA Technologies xGen ® AML Cancer Panel v1.0 | CRISPLD1 |
| #1 | Illumina ® MiSeq ® Reagent Kit v3 | Integrated DNA Technologies xGen ® AML Cancer Panel v1.0 | FAM57B |
| #1 | Illumina ® MiSeq ® Reagent Kit v3 | Integrated DNA Technologies xGen ® AML Cancer Panel v1.0 | SYT15 |
| #1 | Illumina ® MiSeq ® Reagent Kit v3 | Integrated DNA Technologies xGen ® AML Cancer Panel v1.0 | HMCN1 |
| #1 | Illumina ® MiSeq ® Reagent Kit v3 | Integrated DNA Technologies xGen ® AML Cancer Panel v1.0 | PHF6 |
| #1 | Illumina ® MiSeq ® Reagent Kit v3 | Integrated DNA Technologies xGen ® AML Cancer Panel v1.0 | PDCD2L |
| #1 | Illumina ® MiSeq ® Reagent Kit v3 | Integrated DNA Technologies xGen ® AML Cancer Panel v1.0 | TTBK1 |
| #1 | Illumina ® MiSeq ® Reagent Kit v3 | Integrated DNA Technologies xGen ® AML Cancer Panel v1.0 | KIF2B |
| #1 | Illumina ® MiSeq ® Reagent Kit v3 | Integrated DNA Technologies xGen ® AML Cancer Panel v1.0 | LNX1 |
| #1 | Illumina ® MiSeq ® Reagent Kit v3 | Integrated DNA Technologies xGen ® AML Cancer Panel v1.0 | TCEAL3 |
| #1 | Illumina ® MiSeq ® Reagent Kit v3 | Integrated DNA Technologies xGen ® AML Cancer Panel v1.0 | CNTNAP4 |
| #1 | Illumina ® MiSeq ® Reagent Kit v3 | Integrated DNA Technologies xGen ® AML Cancer Panel v1.0 | NAV1 |
| #1 | Illumina ® MiSeq ® Reagent Kit v3 | Integrated DNA Technologies xGen ® AML Cancer Panel v1.0 | PKHD1L1 |
| #1 | Illumina ® MiSeq ® Reagent Kit v3 | Integrated DNA Technologies xGen ® AML Cancer Panel v1.0 | MUC16 |
| #1 | Illumina ® MiSeq ® Reagent Kit v3 | Integrated DNA Technologies xGen ® AML Cancer Panel v1.0 | PKD1L2 |
| #1 | Illumina ® MiSeq ® Reagent Kit v3 | Integrated DNA Technologies xGen ® AML Cancer Panel v1.0 | CSMD3 |
| #1 | Illumina ® MiSeq ® Reagent Kit v3 | Integrated DNA Technologies xGen ® AML Cancer Panel v1.0 | GBP4 |
| #1 | Illumina ® MiSeq ® Reagent Kit v3 | Integrated DNA Technologies xGen ® AML Cancer Panel v1.0 | ARAP2 |
| #1 | Illumina ® MiSeq ® Reagent Kit v3 | Integrated DNA Technologies xGen ® AML Cancer Panel v1.0 | ZC3H18 |
| #1 | Illumina ® MiSeq ® Reagent Kit v3 | Integrated DNA Technologies xGen ® AML Cancer Panel v1.0 | MYOM3 |
| #1 | Illumina ® MiSeq ® Reagent Kit v3 | Integrated DNA Technologies xGen ® AML Cancer Panel v1.0 | GPR112 |
| #1 | Illumina ® MiSeq ® Reagent Kit v3 | Integrated DNA Technologies xGen ® AML Cancer Panel v1.0 | KCNU1 |
| #1 | Illumina ® MiSeq ® Reagent Kit v3 | Integrated DNA Technologies xGen ® AML Cancer Panel v1.0 | FAM47A |
| #1 | Illumina ® MiSeq ® Reagent Kit v3 | Integrated DNA Technologies xGen ® AML Cancer Panel v1.0 | TCEAL6 |
| #1 | Illumina ® MiSeq ® Reagent Kit v3 | Integrated DNA Technologies xGen ® AML Cancer Panel v1.0 | CCDC67 |
| #1 | Illumina ® MiSeq ® Reagent Kit v3 | Integrated DNA Technologies xGen ® AML Cancer Panel v1.0 | XIRP1 |
| #1 | Illumina ® MiSeq ® Reagent Kit v3 | Integrated DNA Technologies xGen ® AML Cancer Panel v1.0 | BMPER |
| #1 | Illumina ® MiSeq ® Reagent Kit v3 | Integrated DNA Technologies xGen ® AML Cancer Panel v1.0 | ASXL1 |
| #1 | Illumina ® MiSeq ® Reagent Kit v3 | Integrated DNA Technologies xGen ® AML Cancer Panel v1.0 | CMYA5 |
| #1 | Illumina ® MiSeq ® Reagent Kit v3 | Integrated DNA Technologies xGen ® AML Cancer Panel v1.0 | UNC5B |
| #1 | Illumina ® MiSeq ® Reagent Kit v3 | Integrated DNA Technologies xGen ® AML Cancer Panel v1.0 | OR8B12 |
| #1 | Illumina ® MiSeq ® Reagent Kit v3 | Integrated DNA Technologies xGen ® AML Cancer Panel v1.0 | PHACTR1 |
| #1 | Illumina ® MiSeq ® Reagent Kit v3 | Integrated DNA Technologies xGen ® AML Cancer Panel v1.0 | CADM2 |
| #1 | Illumina ® MiSeq ® Reagent Kit v3 | Integrated DNA Technologies xGen ® AML Cancer Panel v1.0 | NALCN |
| #1 | Illumina ® MiSeq ® Reagent Kit v3 | Integrated DNA Technologies xGen ® AML Cancer Panel v1.0 | BOD1L |
| #1 | Illumina ® MiSeq ® Reagent Kit v3 | Integrated DNA Technologies xGen ® AML Cancer Panel v1.0 | SLC39A5 |
| #1 | Illumina ® MiSeq ® Reagent Kit v3 | Integrated DNA Technologies xGen ® AML Cancer Panel v1.0 | KSR2 |
| #1 | Illumina ® MiSeq ® Reagent Kit v3 | Integrated DNA Technologies xGen ® AML Cancer Panel v1.0 | FAM154B |
| #1 | Illumina ® MiSeq ® Reagent Kit v3 | Integrated DNA Technologies xGen ® AML Cancer Panel v1.0 | KIAA1267 |
| #1 | Illumina ® MiSeq ® Reagent Kit v3 | Integrated DNA Technologies xGen ® AML Cancer Panel v1.0 | EPHA10 |
| #1 | Illumina ® MiSeq ® Reagent Kit v3 | Integrated DNA Technologies xGen ® AML Cancer Panel v1.0 | FRYL |
| #1 | Illumina ® MiSeq ® Reagent Kit v3 | Integrated DNA Technologies xGen ® AML Cancer Panel v1.0 | ILDR1 |
| #1 | Illumina ® MiSeq ® Reagent Kit v3 | Integrated DNA Technologies xGen ® AML Cancer Panel v1.0 | KRT79 |
| #1 | Illumina ® MiSeq ® Reagent Kit v3 | Integrated DNA Technologies xGen ® AML Cancer Panel v1.0 | FAM5C |
| #1 | Illumina ® MiSeq ® Reagent Kit v3 | Integrated DNA Technologies xGen ® AML Cancer Panel v1.0 | FREM2 |
| #1 | Illumina ® MiSeq ® Reagent Kit v3 | Integrated DNA Technologies xGen ® AML Cancer Panel v1.0 | OR13H1 |
| #1 | Illumina ® MiSeq ® Reagent Kit v3 | Integrated DNA Technologies xGen ® AML Cancer Panel v1.0 | FAM70B |
| #1 | Illumina ® MiSeq ® Reagent Kit v3 | Integrated DNA Technologies xGen ® AML Cancer Panel v1.0 | GSTK1 |
| #1 | Illumina ® MiSeq ® Reagent Kit v3 | Integrated DNA Technologies xGen ® AML Cancer Panel v1.0 | GALNTL4 |
| #1 | Illumina ® MiSeq ® Reagent Kit v3 | Integrated DNA Technologies xGen ® AML Cancer Panel v1.0 | C17orf97 |
| #1 | Illumina ® MiSeq ® Reagent Kit v3 | Integrated DNA Technologies xGen ® AML Cancer Panel v1.0 | CUEDC1 |
| #1 | Illumina ® MiSeq ® Reagent Kit v3 | Integrated DNA Technologies xGen ® AML Cancer Panel v1.0 | OR11H12 |
| #1 | Illumina ® MiSeq ® Reagent Kit v3 | Integrated DNA Technologies xGen ® AML Cancer Panel v1.0 | CLEC18B |
| #1 | Illumina ® MiSeq ® Reagent Kit v3 | Integrated DNA Technologies xGen ® AML Cancer Panel v1.0 | MUC5B |

TABLE 1-continued

Examplary extract of laboratory information listing.

| Lab | Sequencer | Target enrichment technology | Target gene |
|---|---|---|---|
| #1 | Illumina ® MiSeq ® Reagent Kit v3 | Integrated DNA Technologies xGen ® AML Cancer Panel v1.0 | MROH5 |
| #1 | Illumina ® MiSeq ® Reagent Kit v3 | Integrated DNA Technologies xGen ® AML Cancer Panel v1.0 | SBF1P1 |
| #1 | Illumina ® MiSeq ® Reagent Kit v3 | Integrated DNA Technologies xGen ® AML Cancer Panel v1.0 | MIR142 |
| #1 | Illumina ® MiSeq ® Reagent Kit v3 | Integrated DNA Technologies xGen ® AML Cancer Panel v1.0 | EEF1A1P29 |
| #1 | Illumina ® MiSeq ® Reagent Kit v3 | Integrated DNA Technologies xGen ® AML Cancer Panel v1.0 | HSP90B3P |
| #1 | Illumina ® MiSeq ® Reagent Kit v3 | Integrated DNA Technologies xGen ® AML Cancer Panel v1.0 | IGHG3 |
| #1 | Illumina ® MiSeq ® Reagent Kit v3 | Integrated DNA Technologies xGen ® AML Cancer Panel v1.0 | ST13P13 |
| #1 | Illumina ® MiSeq ® Reagent Kit v3 | Multiplicom CFTR MASTR ™ Dx | CFTR |
| #1 | Illumina ® MiSeq ® Reagent Kit v3 | Illumina ® Trusight ® Myeloid Panel | ABL1 |
| #1 | Illumina ® MiSeq ® Reagent Kit v3 | Illumina ® Trusight ® Myeloid Panel | ASXL1 |
| #1 | Illumina ® MiSeq ® Reagent Kit v3 | Illumina ® Trusight ® Myeloid Panel | ATRX |
| #1 | Illumina ® MiSeq ® Reagent Kit v3 | Illumina ® Trusight ® Myeloid Panel | BCOR |
| #1 | Illumina ® MiSeq ® Reagent Kit v3 | Illumina ® Trusight ® Myeloid Panel | BCORL1 |
| #1 | Illumina ® MiSeq ® Reagent Kit v3 | Illumina ® Trusight ® Myeloid Panel | BRAF |
| #1 | Illumina ® MiSeq ® Reagent Kit v3 | Illumina ® Trusight ® Myeloid Panel | CALR |
| #1 | Illumina ® MiSeq ® Reagent Kit v3 | Illumina ® Trusight ® Myeloid Panel | CBL |
| #1 | Illumina ® MiSeq ® Reagent Kit v3 | Illumina ® Trusight ® Myeloid Panel | CBLB |
| #1 | Illumina ® MiSeq ® Reagent Kit v3 | Illumina ® Trusight ® Myeloid Panel | CBLC |
| #1 | Illumina ® MiSeq ® Reagent Kit v3 | Illumina ® Trusight ® Myeloid Panel | CDKN2A |
| #1 | Illumina ® MiSeq ® Reagent Kit v3 | Illumina ® Trusight ® Myeloid Panel | CEBPA |
| #1 | Illumina ® MiSeq ® Reagent Kit v3 | Illumina ® Trusight ® Myeloid Panel | CSF3R |
| #1 | Illumina ® MiSeq ® Reagent Kit v3 | Illumina ® Trusight ® Myeloid Panel | CUX1 |
| #1 | Illumina ® MiSeq ® Reagent Kit v3 | Illumina ® Trusight ® Myeloid Panel | DNMT3A |
| #1 | Illumina ® MiSeq ® Reagent Kit v3 | Illumina ® Trusight ® Myeloid Panel | ETV6/TEL |
| #1 | Illumina ® MiSeq ® Reagent Kit v3 | Illumina ® Trusight ® Myeloid Panel | EZH2 |
| #1 | Illumina ® MiSeq ® Reagent Kit v3 | Illumina ® Trusight ® Myeloid Panel | FBXW7 |
| #1 | Illumina ® MiSeq ® Reagent Kit v3 | Illumina ® Trusight ® Myeloid Panel | FLT3 |
| #1 | Illumina ® MiSeq ® Reagent Kit v3 | Illumina ® Trusight ® Myeloid Panel | GATA1 |
| #1 | Illumina ® MiSeq ® Reagent Kit v3 | Illumina ® Trusight ® Myeloid Panel | GATA2 |
| #1 | Illumina ® MiSeq ® Reagent Kit v3 | Illumina ® Trusight ® Myeloid Panel | GNAS |
| #1 | Illumina ® MiSeq ® Reagent Kit v3 | Illumina ® Trusight ® Myeloid Panel | HRAS |
| #1 | Illumina ® MiSeq ® Reagent Kit v3 | Illumina ® Trusight ® Myeloid Panel | IDH1 |
| #1 | Illumina ® MiSeq ® Reagent Kit v3 | Illumina ® Trusight ® Myeloid Panel | IDH2 |
| #1 | Illumina ® MiSeq ® Reagent Kit v3 | Illumina ® Trusight ® Myeloid Panel | IKZF1 |
| #1 | Illumina ® MiSeq ® Reagent Kit v3 | Illumina ® Trusight ® Myeloid Panel | JAK2 |
| #1 | Illumina ® MiSeq ® Reagent Kit v3 | Illumina ® Trusight ® Myeloid Panel | JAK3 |
| #1 | Illumina ® MiSeq ® Reagent Kit v3 | Illumina ® Trusight ® Myeloid Panel | KDM6A |
| #1 | Illumina ® MiSeq ® Reagent Kit v3 | Illumina ® Trusight ® Myeloid Panel | KIT |
| #1 | Illumina ® MiSeq ® Reagent Kit v3 | Illumina ® Trusight ® Myeloid Panel | KRAS |
| #1 | Illumina ® MiSeq ® Reagent Kit v3 | Illumina ® Trusight ® Myeloid Panel | NRAS |
| #1 | Illumina ® MiSeq ® Reagent Kit v3 | Illumina ® Trusight ® Myeloid Panel | PDGFRA |
| #1 | Illumina ® MiSeq ® Reagent Kit v3 | Illumina ® Trusight ® Myeloid Panel | PHF6 |
| #1 | Illumina ® MiSeq ® Reagent Kit v3 | Illumina ® Trusight ® Myeloid Panel | PTEN |
| #1 | Illumina ® MiSeq ® Reagent Kit v3 | Illumina ® Trusight ® Myeloid Panel | PTPN11 |
| #1 | Illumina ® MiSeq ® Reagent Kit v3 | Illumina ® Trusight ® Myeloid Panel | RAD21 |
| #1 | Illumina ® MiSeq ® Reagent Kit v3 | Illumina ® Trusight ® Myeloid Panel | RUNX1 |
| #1 | Illumina ® MiSeq ® Reagent Kit v3 | Illumina ® Trusight ® Myeloid Panel | SETBP1 |
| #1 | Illumina ® MiSeq ® Reagent Kit v3 | Illumina ® Trusight ® Myeloid Panel | SF3B1 |
| #1 | Illumina ® MiSeq ® Reagent Kit v3 | Illumina ® Trusight ® Myeloid Panel | SMC1A |
| #1 | Illumina ® MiSeq ® Reagent Kit v3 | Illumina ® Trusight ® Myeloid Panel | SMC3 |
| #1 | Illumina ® MiSeq ® Reagent Kit v3 | Illumina ® Trusight ® Myeloid Panel | SRSF2 |
| #1 | Illumina ® MiSeq ® Reagent Kit v3 | Illumina ® Trusight ® Myeloid Panel | STAG2 |
| #1 | Illumina ® MiSeq ® Reagent Kit v3 | Illumina ® Trusight ® Myeloid Panel | TET2 |
| #1 | Illumina ® MiSeq ® Reagent Kit v3 | Illumina ® Trusight ® Myeloid Panel | TP53 |
| #1 | Illumina ® MiSeq ® Reagent Kit v3 | Illumina ® Trusight ® Myeloid Panel | U2AF1 |
| #1 | Illumina ® MiSeq ® Reagent Kit v3 | Illumina ® Trusight ® Myeloid Panel | WT1 |
| #1 | Illumina ® MiSeq ® Reagent Kit v3 | Illumina ® Trusight ® Myeloid Panel | ZRSR2 |
| #2 | Ion PGM ™ 318 ™ | Multiplicom BRCA MASTR ™ Dx | BRCA1 |
| #2 | Ion PGM ™ 318 ™ | Multiplicom BRCA MASTR ™ Dx | BRCA2 |

Next Generation Sequencing Analysis #1—Integrated DNA Technologies xGen® AML Cancer Panel and Illumina® MiSeq® NGS Sequencing In the first analysis workflow for Lab #1, the genomic data analyzer 120 receives 600 an NGS sequencing analysis request from Lab #1, comprising two raw sequencing files from an Illumina sequencer, each file corresponding to a different reading direction (3' to 5' and 5' to 3' respectively) of the pair-ended reads. The genomic data analyzer 120 identifies 611 a first set of characteristics of the genomic analysis experiment by searching for headers, sequence patterns, adapter patterns and/or gene context patterns in the raw sequencing input files that match one of the laboratory information listings. In this first analysis workflow from Lab #1, the genomic data analyzer 120 identifies 611 the sequencer technology identifier as Illumina MiSeq® Reagent Kit V3 from the laboratory information listing for Lab #1, confirmed by the pair of two FASTQ files, which comprise the Illumina headers and Illumina specific adapter patterns.

The genomic data analyzer 120 also derives from the laboratory information listing for Lab #1 that the target enrichment technology is either to the Integrated DNA Technologies xGen® AML Cancer Panel v1.0, the Illumina Trusight® myeloid sequencing panel, or the Multiplicom CFTR MASTR™ Dx assay. The genomic data analyzer 120 may then search the FASTQ file for assay-specific sequence patterns and identifies 611 accordingly whether a probe-based or an amplicon-based target enrichment techonology has been used in the experiment. The genomic data analyzer 120 identifies 611 the target enrichment technology identifier as Integrated DNA Technologies xGen® AML Cancer Panel v1.0, and the genomic context identifier as the list of 260 genes covered by this specific panel version, as can be discriminated by searching in the raw sequencing data files for xGen specific adaptor patterns as well as the gene context specific patterns for at least some of the 260 genes covered by this panel. The latter search may also help discriminate between different versions of the assay, as a laboratory may progressively replace certain assays with more recent versions, possibly subject to less biological biases, so that the genomic data analyzer 120 sequence alignment module 121 and/or variant calling module 122 may be configured accordingly to maximize the efficiency and the accuracy of genomic variant analysis.

As a function of at least one of these first characteristics, such as the Illumina sequencing technology identifier and the Integrated DNA Technologies xGen® AML Cancer Panel v1.0 target enrichment technology identifier, the genomic data analyzer 120 configures 631 the data alignment module 121 to execute 632 a first raw data alignment algorithm. The data alignment module 121 first executes 632 pre-processing steps such as removing the xGen panel specific adapters from the reads in accordance with the Integrated DNA Technologies xGen® AML Cancer Panel v1.0 target enrichment technology identifier.

The data alignment module 121 then aligns 632 to a reference genomic sequence, with a raw data alignment algorithm as known to those skilled in the art of bioinformatics, the pre-processed raw sequencing data to produce an alignment data file. Standard algorithms such as Bowtie2 or BWA that have been optimized for fast processing of numerous genomic data sequencing reads may be used, but other embodiments are also possible.

The resulting alignment data file may be represented as one or several files in BAM or SAM format, but other embodiments are also possible, in particular the data alignment module 121 may also execute 632 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 further identifies 612 a second set of characteristics such as soft clip patterns overlapping genomic regions of potential clinical relevance. Soft clip patterns correspond to sequencing data at the 5' or 3' boundaries of the reads that could not be properly aligned by the data alignment module 121 raw alignment algorithms 632. Soft clipped alignments are specifically marked in the CIGAR string of the alignment data file, so the corresponding patterns can be easily identified after data alignment 632. As known to those skilled in the art of Next Generation Sequencing, soft clipping information may then be re-mapped in the genomic analysis workflow with specific algorithms in order to further detect structural variants of potential clinical relevance.

As a function of at least one of the first set of characteristics, such as genomic context identifier, and at least one of the second set of characteristics, such as the presence of certain soft clip patterns, the genomic data analyzer 120 automatically configures 633 the data alignment module 121 to execute 634 a data re-alignment algorithm to specifically refine certain regions of the raw alignment data, in order to produce a refined alignment data file. Examples of such algorithms have been described for instance by Suzuki et al. in *"ClipCrop: a tool for detecting structural variations with single-base resolution using soft-clipping information"*, BMC Bioinformatics 2011 12(Suppl 14):S7 and by Schröder et al in *"Socrates: identification of genomic rearrangements in tumour genomes by re-aligning soft clipped reads"*, Bioinformatics (2014), but other embodiments are also possible. In particular the most efficient re-alignment algorithm may be automatically configured 633 by the proposed genomic data analyzer 120 as a function of both the genomic context and the raw alignment soft clip patterns.

The genomic data analyzer 120 further identifies 613 in the refined alignment data a third set of characteristics such as complex patterns and/or homopolymer patterns that, if present, may require a specific configuration of the variant calling module 122. In particular different variant calling algorithms may be applied on different regions, for instance a specific variant calling method may be called on ALU repeats that have been associated with certain prognosis of AML (So et al, *"MLL self fusion mediated by Alu repeat homologous recombination and prognosis of AML-M4/M5 subtypes."* Cancer Res. 1997 Jan. 1; 57(1): 117-22). The genomic data analyzer 120 thus configures 641 the variant calling module 122 to execute 642 certain variant calling algorithms on the refined alignment data, depending on characteristics such as the genomic context and the presence of challenging data alignment patterns.

The variant calling module 122 calls 642 variants on the refined alignment data to produce a first VCF file. In some cases, the resulting variants may not be accurate enough to be reported by the genomic data analyzer 120. The genomic data analyzer 120 may thus identify 614 a fourth set of characteristics such as the need for variant phasing from the initial variant calling results, and configure 643 the variant calling module 122 to refine 644 the variant calling results, depending on characteristics such as for instance whether adjacent variants can be supported by the same reads.

The genomic data analyzer 120 finally reports 650 detected genomic variants with optimized sensitivity and specificity in response to the Lab #1 first genomic analysis request.

Next Generation Sequencing Analysis #2—Multiplicom CFTR MASTR™ Dx Assay and Illumina® MiSeq® NGS Sequencing In the second analysis workflow issued for Lab #1, the genomic data analyzer 120 receives 600 an NGS sequencing analysis request from Lab #1, comprising two raw sequencing files from an Illumina sequencer, each file corresponding to a different reading direction (3' to 5' and 5' to 3' respectively) of the pair-ended reads. The genomic data analyzer 120 identifies 611 a first set of characteristics of the genomic analysis experiment by searching for headers, sequence patterns, adapter patterns and/or gene context patterns in the raw sequencing input files that match one of the laboratory information listings. In this first analysis workflow from Lab #1, the genomic data analyzer 120 identifies 611 the sequencer technology identifier as Illumina MiSeq® Reagent Kit V3 from the laboratory information listing for Lab #1, confirmed by the pair of two FASTQ files, which comprise the Illumina headers and Illumina specific adapter patterns.

The genomic data analyzer 120 also derives from the laboratory information listing for Lab #1 that the target enrichment technology is either to the Integrated DNA Technologies xGen® AML Cancer Panel v1.0, the Illumina Trusight® myeloid sequencing panel, or the Multiplicom CFTR MASTR™ Dx assay. The genomic data analyzer 120 may then search the FASTQ file for assay-specific sequence patterns and identifies 611 accordingly whether a probe-based or an amplicon-based target enrichment techonology has been used in the experiment. The genomic data analyzer 120 identifies 611 the target enrichment technology identifier as Multiplicom CFTR MASTR™ Dx assay, and the genomic context identifier as the CFTR gene covered by this 30 bp-long specific amplicon-based kit, as can be discriminated by searching in the raw sequencing reads for the specific Multiplicom primers patterns associated with this assay and identifying the specific Multiplicom sequencing adaptor patterns.

As a function of at least one of these first characteristics, such as the Illumina sequencing technology identifier and the Multiplicom CFTR MASTR™ Dx target enrichment technology identifier, the genomic data analyzer 120 configures 631 the data alignment module 121 to execute 632 a first raw data alignment. The data alignment module 121 may also execute 632 pre-processing steps such as removing the Multiplicom specific adapters from the reads and/or merging the pair-ended files into a single merged file.

The data alignment module 121 aligns 632 to a reference genomic sequence, with a raw data alignment algorithm as known to those skilled in the art of bioinformatics, the pre-processed raw sequencing data to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 632 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 may then automatically derive 612 a second set of characteristics from the results of data alignment 430, such as a specific data alignment pattern requiring refinement of the alignment and/or the variant calling algorithms. The genomic data analyzer may in particular detect the presence of alignment mismatches especially at the beginning and/or the end of the reads ("soft clipping"), as may be due to primer mispriming. This frequent bias in amplicon-based technologies may indeed cause either:

False positives, when a mispriming artifact is present in enough reads to be misaligned to the reference genome, which will cause a wrong variant calling 642 interpretation as a SNP in the DNA sample;

False negatives, when the alignment module 121 cannot discriminate between mispriming artifacts in certain reads and the correct amplicon data in other reads, causing the corresponding regions to be soft clipped by the data alignment module 121, which will in turn cause the variant calling 642 to miss possible variants of pathological relevance in the correct amplicon data.

Soft clip patterns correspond to sequencing data at the 5' or 3' boundaries of the reads that could not be properly aligned by the data alignment module 121 raw alignment algorithms 632. Soft clipped alignments are specifically marked in the CIGAR string of the alignment data file, so the corresponding patterns can be easily identified after data alignment 632. As known to those skilled in the art of Next Generation Sequencing, soft clipping information may then be re-mapped in the genomic analysis workflow with specific algorithms in order to further detect structural variants of potential clinical relevance.

The genomic data analyzer 120 may thus automatically identify 612 the reads with soft clipping regions, from the results of the data alignment 632, and configure 633 the data alignment module 121 to operate a further data re-alignment 634 on those reads specifically by taking into account the primer anchors information corresponding to the specific DNA enrichment technology, here the Multiplicom CFTR MASTR™ Dx list of primer sequences, in the alignment algorithm. As will be apparent to those skilled in the art of bioinformatics, a more robust algorithm than Bowtie2 or BWA may be used specifically on those regions, even if less computationally efficient. Indeed, only a subset of the whole NGS data needs to be re-aligned this way and the proposed workflow is fully automatized, so the overall computational efficiency performance of the genomic data analyzer 120 is not be significantly impacted, while this data re-alignment refinement automation enables to increase the specificity and sensitivity of the genomic data analyzer 120 to be comparable to that obtained with manual trial-and-errors setups of the prior art research practice. Examples of such algorithms have been described for instance by Suzuki et al. in "*ClipCrop: a tool for detecting structural variations with single-base resolution using soft-clipping information*", *BMC Bioinformatics* 2011 12(Supp114):S7 and by Schröder et al in "*Socrates: identification of genomic rearrangements in tumour genomes by re-aligning soft clipped reads*", *Bioinformatics* (2014), but other embodiments are also possible. In particular the most efficient re-alignment algorithm may be automatically configured 633 by the proposed genomic data analyzer 120 as a function of both the genomic context and the raw alignment data soft clip patterns.

Depending on the genomic context identifier, the genomic data analyzer 120 may also identify from the alignment data the presence of some regions that are particularly challenging to align, such as homopolymer regions or regions with specific repeat patterns. As known to those skilled in the art of genomics, some of the human genome mutations causing CFTR are characterized by a shorter repeat of the T nucleotide (poly T tract) in conjunction with a longer string of TG repeats (TG tract). Proper alignment of corresponding next generation sequencing reads is particularly challenging as those multiple repeats cause alignment ambiguities. FIG. 7 shows an example of reads that cannot be independently aligned to the reference sequence Ref by a standard algorithm which aligns the reads independently from each other, such as Bowtie2 or BWA in such a genomic context. The genomic data analyzer 120 may thus automatically identify 612 from the results of the raw data alignment 632 a specific genomic context requiring refinement on the reads overlapping those ambiguous regions. The genomic data analyzer 120 may accordingly configure 633 the data alignment module 121 to operate a further data re-alignment 634 on those reads to identify other possible alignment solutions, such as for instance by taking into account the PCR error rate and comparing reads to each other. The correct results as derived from an embodiment of such a more robust alignment solution are represented in FIG. 8.

The genomic data analyzer 120 may then use the target enrichment technology identifier to configure 641 the variant calling module 122 to execute different variant calling algorithms in accordance with the initially identified genomic context identifier (e.g. CTFR) and the specific genomic context refinement identified from the raw alignment results (e.g. the presence of certain Poly-T/TG patterns in the data). The variant calling module 122 calls 642 variants on the refined alignment data to produce a first VCF file. In some cases, the resulting variants may not be accurate enough to be reported by the genomic data analyzer 120. The genomic data analyzer 120 may thus identify 614 a fourth set of characteristics such as the need for variant phasing from the initial variant calling results, and configure 643 the variant calling module 122 to refine 644 the variant calling data, depending on characteristics such as whether the adjacent variants are presented in the same reads. The genomic data analyzer 120 finally reports 650 detected genomic variants with optimized sensitivity and specificity in response to the Lab #1 second genomic analysis request.

Next Generation Sequencing Analysis #3—Illumina® Trusight® Myeloid Panel and Illumina® MiSeq® NGS Sequencing In the third analysis workflow issued for Lab #1, the genomic data analyzer 120 receives 600 an NGS sequencing analysis request from Lab #1, comprising two raw sequencing files from an Illumina sequencer, each file corresponding to a different reading direction (3' to 5' and 5' to 3' respectively) of the pair-ended reads. The genomic data analyzer 120 identifies 611 a first set of characteristics of the genomic analysis experiment by searching for headers, sequence patterns, adapter patterns and/or gene context patterns in the raw sequencing input files that match one of the laboratory information listings. In this first analysis workflow from Lab #1, the genomic data analyzer 120 identifies 611 the sequencer technology identifier as Illumina MiSeq® Reagent Kit V3 from the laboratory information listing for Lab #1, confirmed by the pair of two FASTQ files, which comprise the Illumina headers and Illumina specific adapter patterns.

The genomic data analyzer 120 also derives from the laboratory information listing for Lab #1 that the target enrichment technology is either to the Integrated DNA Technologies xGen® AML Cancer Panel v1.0, the Illumina Trusight® myeloid sequencing panel, or the Multiplicom CFTR MASTR™ Dx assay. The genomic data analyzer 120 may then search the FASTQ file for assay-specific sequence patterns and identifies 611 accordingly whether a probe-based or an amplicon-based target enrichment techonology has been used in the experiment. The genomic data analyzer 120 identifies 611 the target enrichment technology identifier as the Illumina Trusight® myeloid sequencing panel, and the genomic context identifier as the list of 54 genes covered by this specific amplicon-based panel, as can be discriminated by searching in the raw sequencing reads for the specific 22 bp- to 30 bp-long primers patterns associated with this assay and identifying the specific Illumina sequencing adaptor patterns.

As a function of at least one of these first characteristics, such as the Illumina sequencing technology identifier and the Illumina Trusight® myeloid sequencing panel target enrichment technology identifier, the genomic data analyzer 120 configures 631 the data alignment module 121 to execute 632 a first raw data alignment. The data alignment module 121 may also execute 632 pre-processing steps such as:

removing the Illumina Trusight® myeloid sequencing panel specific adapters from the reads;
merging the pair-ended raw sequencing FASTQ files into a single merged file.

As known to those skilled in the art of bioinformatics, the SHERA or PEAR software may be used for merging the pair-ended reads in their overlapping parts over the DNA fragment. A number of improvements have been proposed in the literature to increase the reads merging algorithm robustness to next generation sequencing detection failures, by using certain heuristics in combining the pair-ended data into a more accurate merged read data. For instance in "*AdapterRemoval: easy cleaning of next generation sequencing reads*", BMC Research Notes 2012 5:337, S. Lindgreen proposed to represent the quality scores Q for the overlapping region as a position specific scoring matrix (PSSM). At each position, the probability for the read nucleotide may be computed as $P_r = 1-10^{-Q/10}$ while the probability for the three other nucleotides can be estimated as $P_n = 1/3 * 10^{-Q/10}$. The probabilities for the two reads may then be combined into a single re-estimated probability distribution for the overlapping region. A further improvement may consist in using a higher order probabilistic model for combining the quality scores, for instance by using a sliding window to also take into account quality information from adjacent positions rather than scoring the quality independently at each nucleotide position. These improvements are of particular relevance in somatic analyses, as the variant mutations may be found only in a subset of the overall DNA and may thus remain undetected in the overall NGS detection data biases if the latter is not further optimized by more robust alignment pre-processing algorithms. In AML diagnosis, the FLT3-ITD region is particularly challenging to sequence because of its inherent tandem duplications in mutations of pathological relevance. In that specific context some of the reads do not merge well, however it may still be possible to extract some data from some of the remaining, unmerged reads with certain quality patterns. The genomic data analyzer 120 is thus adapted to automatically select and configure 631 the most suitable reads merging pre-processing algorithm for the data alignment module 121 based at least one characteristic of the input data that may be easily extracted from the raw NGS files, here the genomic context identifier listing of FLT3 for the Illumina Trusight myeloid panel.

The data alignment module 121 aligns 632 to a reference genomic sequence, with a raw data alignment algorithm as known to those skilled in the art of bioinformatics, the pre-processed raw sequencing data to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 632 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 further identifies 612 a second set of characteristics such as:

soft clip patterns overlapping genomic regions of potential clinical relevance;

probe extension patterns introduced by Illumina amplicon-based technology, to be trimmed out from the alignment data prior to variant calling.

In most prior art genomic analysis practice, the NGS sequencing reads corresponding to the PCR amplification or probe extension primers as well as the sequencing adapters are removed from the raw sequencing data prior to initial alignment 632, and a diversity of pre-processing algorithm software have been developed accordingly in genomics research practice. These approaches are however suboptimal in next generation sequencing combined with targeted amplicon-based enrichment technologies, which cause edge effects in sequencing near the amplicon boundaries. In "*Edge effects in calling variants from targeted amplicon sequencing*", BMC Genomics 2014, 15:1073, V. Satya and J. DiCarlo thus suggested to keep at least a few bases of the primer at both ends of the reads prior to alignment, and only trimming them after alignment, before variant calling. In a possible embodiment, the proposed genomic data analyzer 120 may thus be further adapted not to trim the primer anchors from the raw sequencing data prior to raw alignment 632. The proposed genomic data analyzer is then further adapted to automatically select and configure 633 the most suitable primer trimming algorithm for the data alignment module 121, based on at least one characteristic of the first set of characteristics of the input data such as the targeted enrichment technology identifier and/or the genomic context identifier, and at least one characteristic of the second set of characteristics, such as the presence of certain probe extension patterns in the raw alignment data. The genomic data analyzer 120 may for instance refer to a pre-defined list of extension probes as specifically designed by the provider of the target enrichment technology used by Lab #1, here the Illumina Trusight myeloid panel, to search for known extension probes associated with this target enrichment technology in the raw alignment data file.

In addition to the presence of certain extension probe patterns, the genomic data analyzer 120 may further identify 612 the presence of soft clip patterns overlapping genomic regions of potential clinical relevance as part of the second set of characteristics to trigger a more optimal configuration of the data alignment module 121 and/or the variant calling module 122. Soft clip patterns correspond to sequencing data at the 5' or 3' boundaries of the reads that could not be properly aligned by the data alignment module 121 raw alignment algorithms 632. Soft clipped alignments are specifically marked in the CIGAR string of the alignment data file, so the corresponding patterns can be easily identified after data alignment 632. As known to those skilled in the art of Next Generation Sequencing, soft clipping information may then be re-mapped in the genomic analysis workflow with specific algorithms in order to further detect structural variants of potential clinical relevance. As a function of at least one of the first set of characteristics, such as genomic context identifier, and at least one of the second set of characteristics, such as the presence of certain soft clip and/or probe extension primers raw alignment data patterns, the genomic data analyzer 120 automatically configures 633 the data alignment module 121 to execute 634 a data re-alignment algorithm to specifically refine certain regions of the raw alignment data, in order to produce a refined alignment data file. Examples of such algorithms have been described for instance by Suzuki et al. in "*ClipCrop: a tool for detecting structural variations with single-base resolution using soft-clipping information*", BMC Bioinformatics 2011 12(Suppl14):S7 and by Schröder et al in "*Socrates: identification of genomic rearrangements in tumour genomes by re-aligning soft clipped reads*", Bioinformatics (2014), but other embodiments are also possible. In particular the most efficient re-alignment algorithm may be automatically configured 633 by the proposed genomic data analyzer 120 as a function of both the genomic context and the raw alignment data patterns.

The genomic data analyzer 120 further identifies 613 in the refined alignment data a third set of characteristics such as complex patterns and/or homopolymer genomic context patterns that, if present, may require a specific configuration of the variant calling module 122. In particular different variant calling algorithms may be applied on different regions. For example, the FLT3 tandem duplication may prevent the merging of the pair-ended reads, as they can no longer overlap each other due to the pattern duplication. Unmerged reads may be specifically mapped by a dedicated algorithm in the alignment data refinement step 634. Then, if there is an overrepresented ratio of soft-clip patterns or other patterns of interest in the refined data alignment data for those unmerged reads, the presence of the corresponding genomic context identifier in the third set of characteristics triggers the variant calling module 122 to execute a different variant calling 642 algorithm that takes both the merged and the unmerged reads into account in the genomic context refinement regions associated with those complex patterns. The genomic data analyzer 120 thus configures 641 the variant calling module 122 to execute 642 certain variant calling algorithms on the refined alignment data, depending on characteristics such as the genomic context and the presence of challenging patterns.

The variant calling module 122 calls 642 variants on the refined alignment data to produce a first VCF file. In some cases, the resulting variants may not be accurate enough to be reported by the genomic data analyzer 120. The genomic data analyzer 120 may thus identify 614 a fourth set of characteristics such as the need for variant phasing from the initial variant calling results, and configure 643 the variant calling module 122 to refine 644 the variant calling data, depending on variant calling refinement characteristics such as whether the adjacent variants are presented in the same reads.

The genomic data analyzer 120 finally reports 650 detected genomic variants with optimized sensitivity and specificity in response to the Lab #1 first genomic analysis request.

Next Generation Sequencing Analysis #4—Multiplicom BRCA Hereditary Cancer MASTR™ Plus Assay and Ion PGM™318™

In the fourth analysis workflow issued for Lab #2, the genomic data analyzer 120 receives 600 an NGS sequencing analysis request from Lab #2, comprising one raw sequencing files from an Ion Torrent sequencer in the uncompressed BAM file format.

The genomic data analyzer 120 identifies 611 a first set of characteristics of the genomic analysis experiment by searching for headers, sequence patterns, adapter patterns and/or gene context patterns in the raw sequencing input file that match one of the laboratory information listings. In this first analysis workflow from Lab #2, the genomic data analyzer 120 identifies 611 the sequencer technology identifier as Ion PGM™ 318™ from the laboratory information listing for Lab #2, which is consistent with the uncompressed BAM file format received from Lab #2.

The genomic data analyzer 120 also derives from the laboratory information listing for Lab #2 that the target enrichment technology is the Multiplicom BRCA MASTR™ Dx assay. The genomic data analyzer 120 may also search the raw sequencing input file for assay-specific sequence patterns and identifies 611 accordingly that an amplicon-based target enrichment technology has been used in the experiment. The genomic data analyzer 120 identifies 611 the target enrichment technology identifier as Multiplicom BRCA MASTR™ Dx assay, and the genomic context identifier as the set of 2 genes covered by this specific amplicon-based kit, as can be also confirmed by searching in the raw sequencing reads for the specific 289 bp- to 430 bp-long Multiplicom primers patterns associated with this assay and identifying the specific Multiplicom sequencing adaptor patterns.

As a function of at least one of these first characteristics, such as the IonTorrent sequencing technology identifier and the Multiplicom BRCA MASTR™ Dx target enrichment technology identifier, the genomic data analyzer 120 configures 631 the data alignment module 121 to execute 632 a first raw data alignment. The data alignment module 121 may also execute 632 pre-processing steps such as removing the Multiplicom specific adapters from the reads.

The data alignment module 121 aligns 632 to a reference genomic sequence, with a raw data alignment algorithm as known to those skilled in the art of bioinformatics, the pre-processed raw sequencing data to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 632 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 may then automatically derive 612 a second set of characteristics from the results of data alignment 430, such as a specific data alignment pattern requiring refinement of the alignment and/or the variant calling algorithms. The genomic data analyzer may in particular detect the presence of alignment mismatches especially at the beginning and/or the end of the reads ("soft clipping"), as may be due to primer mispriming. This frequent bias in amplicon-based technologies may indeed cause either:

False positives, when a mispriming artifact is present in enough reads to be misaligned to the reference genome, which will cause a wrong variant calling 642 interpretation as a SNP in the DNA sample;

False negatives, when the alignment module 121 cannot discriminate between mispriming artifacts in certain reads and the correct amplicon data in other reads, causing the corresponding regions to be soft clipped by the data alignment module 121, which will in turn cause the variant calling 642 to miss possible variants of pathological relevance in the correct amplicon data.

Soft clip patterns correspond to sequencing data at the boundaries of the reads that could not be properly aligned by the data alignment module 121 raw alignment algorithms 632. Soft clipped alignments are specifically marked in the CIGAR string of the alignment data file, so the corresponding patterns can be easily identified after data alignment 632. As known to those skilled in the art of Next Generation Sequencing, soft clipping information may then be re-mapped in the genomic analysis workflow with specific algorithms in order to further detect structural variants of potential clinical relevance.

The genomic data analyzer 120 may thus automatically identify 612 the reads with soft clipping regions, from the results of the data alignment 632, and configure 633 the data alignment module 121 to operate a further data re-alignment 634 on those reads specifically by taking into account the primer anchors information corresponding to the specific DNA enrichment technology, here the Multiplicom BRCA MASTR™ Dx list of primer sequences, in the alignment algorithm. As will be apparent to those skilled in the art of bioinformatics, a more robust algorithm than Bowtie2 or BWA may be used specifically on those regions, even if less computationally efficient. Indeed, only a subset of the whole NGS data needs to be re-aligned this way and the proposed workflow is fully automatized, so the overall computational efficiency performance of the genomic data analyzer 120 is not be significantly impacted, while this data re-alignment refinement automation enables to increase the specificity and sensitivity of the genomic data analyzer 120 to be comparable to that obtained with manual trial-and-errors setups of the prior art research practice. Examples of such algorithms have been described for instance by Suzuki et al. in "ChpCrop: a tool for detecting structural variations with single-base resolution using soft-clipping information", BMC Bioinformatics 2011 12(Supp114):S7 and by Schröder et al in "Socrates: identification of genomic rearrangements in tumor genomes by re-aligning soft clipped reads", Bioinformatics (2014), but other embodiments are also possible.

Depending on the genomic context identifier, the genomic data analyzer 120 may also identify from the refined alignment data the presence of some regions that are particularly challenging to infer the mutation status, such as homopolymer regions or regions with specific repeat patterns, as can be found in particular in the BRCA1 and BRCA2 genomic contexts.

Depending on the sequencing technology identifier, here Ion Torrent PGM™ for Lab #2, the genomic data analyzer 120 may also determine the need for a dedicated variant calling algorithm configuration, as the use of relatively short (200 bp-long) sequencing reads in this technology and its sensitivity to homopolymer sequencing errors raise specific next generation sequencing data analysis challenges.

The genomic data analyzer 120 may thus use the target enrichment technology identifier to configure 641 the variant calling module 122 to execute different variant calling algorithms depending on:

the genomic context identifiers (e.g. BRCA1, BRCA2 . . . );

the specific genomic context refinement identified from the raw alignment and/or the refined alignment results (e.g. the presence of certain homopolymer patterns in the data);

the sequencing technology identifier. Indeed, Ion Torrent sequencing is known to provide accurate results in SNP detection, but high false positive and false negative rates when searching for INDELs in the BRCA1 and BRCA2 genomic context when using a conventional variant calling algorithm such as GTAK or SAMTools. Examples of such algorithms have been described for instance by Yeo et al, "Evaluation and optimisation of indel detection workflows for ion torrent sequencing of the BRCA1 and BRCA2 genes", BMC Genomics 2014 15:516, but other embodiments are also possible.

The variant calling module 122 calls 642 variants on the refined alignment data to produce a first VCF file. In some cases, the resulting variants may not be accurate enough to be reported by the genomic data analyzer 120. The genomic data analyzer 120 may thus identify 614 a fourth set of characteristics such as the need for variant phasing from the initial variant calling results, and configure 643 the variant calling module 122 to refine 644 the variant calling data, depending on characteristics such as variant calling refinement characteristics such as whether the adjacent variants are presented in the same reads.

The genomic data analyzer 120 finally reports 650 detected genomic variants with optimized sensitivity and specificity in response to the Lab #2 second genomic analysis request.

Experimental Results

FIG. 9 shows an improvement of the specificity of variant detection in a genomic analysis experiment conducted respectively with a conventional bioinformatics workflow of the prior art (FIG. 9*a*) and an embodiment of the proposed automated bioinformatics workflow optimization (FIG. 9*b*). FIG. 9*a*) illustrates a false positive variant detection retrieved by conventional variant calling on the raw alignment data a standard alignment algorithm on next generation sequencing reads, whereas FIG. 9*b*) illustrates the proper genomic sequence alignment without the false positive variant detection as retrieved by the proposed genomic data analyzer 120, which automatically identified the presence of challenging soft clipping patterns in the raw alignment data and configured the data alignment module 121 to execute an optimized alignment algorithm to produce a refined alignment data file. As can be seen in the results from FIG. 9*b*), no more false positive variant is detected, without requiring a manual configuration or a specific configuration request from the sourcing laboratory.

The proposed genomic data analyzer 120 enables to serve thousands of sourcing laboratories, processing the data from hundreds of thousands of clinical samples processed with multiple enrichment technologies and sequenced on a diversity of next generation sequencing (NGS) platforms. By utilizing this rich data set coupled with the proposed genomic data analysis methods, robust and accurate variant calling results can be reached with the proposed automated workflow sensitivity and specificity matching that of manual algorithm configuration and fine-tuning by bioinformatics experts, as shown in FIG. 9. Moreover, the proposed fully automated genomic data analyzer 120 system can be deployed, tested and validated without requiring individual setup and fine-tuning of their specific NGS genomic analysis workflow by the sourcing laboratories, and will thus accelerate access to personalized and precision medicine for hundreds of thousands of patients in Europe and worldwide. A further advantage of the proposed methods and systems is that it facilitates backward and forward compatibility. Adding new laboratories with new characteristics to be supported does not require to update the legacy laboratory sourcing requests as required with prior art methods based upon explicit metadata communications.

Other Embodiments and Applications

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

Although the detailed description above contains many specific details, these should not be construed as limiting the scope of the embodiments but as merely providing illustrations of some of several embodiments. While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, units, or mechanisms. Modules or units may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A computer-implemented method to analyze next generation sequencing genomic data from a sourcing laboratory, comprising:

receiving, with a processor, via a communication network, a next generation sequencing analysis request from a sourcing laboratory, the next generation sequence request generated via a laboratory computing infrastructure of the sourcing laboratory, the next generation sequencing request comprising at least a raw sequencing data file and a sourcing laboratory identification;

identifying, with a processor, a first set of characteristics associated with the next generation sequencing analysis request, the first set of characteristics comprising at least a target enrichment technology identifier, a sequencing technology identifier, and a genomic context identifier;

configuring, with a processor, a data alignment module to align the raw sequencing data file in accordance with at least one characteristic of said first set of characteristics;

aligning, with the data alignment module processor, the raw sequencing data to a genomic sequence to produce a raw alignment file;

identifying, with a processor, a second set of characteristics associated with the alignment data from the raw alignment data file, the second set of characteristics comprising at least a data alignment pattern identifier;

configuring, with a processor, the data alignment module to refine at least one subset of the input raw sequencing data in accordance with at least one characteristic of the first set of characteristics and at least one characteristic of the second set of characteristics;

refining with the configured data alignment module processor, the subset of the raw alignment data to produce a refined alignment data file, wherein refining the subset of the input raw alignment data to produce the refined alignment data file comprises re-aligning a subset of the raw alignment data file;

configuring, with a processor, a variant calling module to identify variants associated with the raw sequencing data file in accordance with at least one characteristic of said first set of characteristics and at least one characteristic of the second set of characteristics; and identifying genomic variants, with the variant calling module processor, in the refined alignment data file.

2. The computer-implemented method of claim 1, wherein the sourcing laboratory identification comprises authentication credentials.

3. The computer-implemented method of claim 1, wherein the sourcing laboratory identification comprises a laboratory identifier metadata.

4. The computer-implemented method of claim 1, further comprising reporting, with a processor, the identified genomic variants to the sourcing laboratory.

5. The computer-implemented method of claim 1, wherein refining the subset of the input raw alignment data comprises extracting a subset of the raw alignment data file, refining this subset, and merging the resulting re-alignment datafile with the raw alignment data file to produce the refined alignment data file.

6. The computer-implemented method of claim 1, further comprising:
configuring, with a processor, the variant calling module to identify variants associated with the refined alignment data in accordance with at least one characteristic of the first set of characteristics and one characteristic of the second set of characteristics;
identifying genomic variants, with the configured variant calling module processor, in the refined alignment data.

7. The computer-implemented method of claim 6, further comprising reporting, with a processor, the identified genomic variants to the sourcing laboratory.

8. The computer-implemented method of claim 1, further comprising:
identifying, with a processor, a third set of characteristics associated with the alignment data from the refined alignment data file, the third set of characteristics comprising at least a genomic context identifier;
configuring, with a processor, a variant calling module to identify variants associated with the refined alignment data in accordance with at least one characteristic of the first set of characteristics, at least one characteristic of the second set of characteristics, and at least one characteristic of the third set of characteristics;
identifying genomic variants, with the configured variant calling module processor, in the refined alignment data.

9. The computer-implemented method of claim 8, further comprising:
reporting, with a processor, the identified genomic variants to the sourcing laboratory.

10. The computer-implemented method of claim 8 further comprising:
identifying, with a processor, a fourth set of characteristics associated with the detected genomic variants, the fourth set of characteristics comprising at least a variant calling refinement identifier;
configuring, with a processor, the variant calling module to identify variants associated with the refined alignment data in accordance with at least one characteristic of the first set of characteristics, at least one characteristic of the second set of characteristics, at least one characteristic of the third set of characteristics and at least one characteristic of the fourth set of characteristics;
identifying refined genomic variants, with the configured variant calling module processor, in the refined alignment data and the detected genomic variants, to produce a refined set of genomic variants.

11. The computer-implemented method of claim 10, further comprising reporting, with a processor, the identified set of genomic variants to the sourcing laboratory.

12. The computer-implemented method of claim 8, wherein the genomic context identifier comprises a homopolymer pattern, a pseudogene pattern, a short tandem repeat polymorphic site pattern, a variable number of tandem repeat site patterns, and/or a complex genomic pattern with multiple repeats.

13. The computer-implemented method of claim 1, wherein the data alignment pattern identifier is a sub-sequence pattern in the raw aligned data.

14. The computer-implemented method of claim 13, further comprising identifying that the enrichment technology is amplicon-based and wherein the sub-sequence pattern comprises primer patterns to be trimmed out of the alignment data.

15. The computer-implemented method of claim 14, further comprising identifying that the enrichment technology is an amplicon-based assay and wherein the sub-sequence pattern comprises assay-dependent patterns specific to the amplicon-based target enrichment technology primer design, such as miss-priming patterns or primer dimmers.

16. The computer-implemented method of claim 14, wherein the sub-sequence pattern comprises a homopolymer pattern, a pseudogene pattern, a short tandem repeat polymorphic site pattern, a variable number of tandem repeat site patterns, and/or a complex genomic pattern with multiple repeats.

17. A computer-implemented method to analyze next generation sequencing genomic data from a plurality of sourcing laboratories, comprising:
receiving, with a processor, via a communication network, a next generation sequencing analysis request from each of the plurality of sourcing laboratories, the next generation sequence request generated via a laboratory computing infrastructure of each of the plurality of sourcing laboratories, the next generation sequencing request comprising at least a raw next generation sequencing data file and the sourcing laboratory identification;
identifying, with a processor, a first set of characteristics associated with the next generation sequencing analysis request, the first set of characteristics comprising at least a target enrichment technology identifier, a sequencing technology identifier, and a genomic context identifier;
configuring, with a processor, a data alignment module to align the input raw sequencing data file in accordance with at least one characteristic of said first set of characteristics;
aligning, with the data alignment module processor, the input sequencing data to a genomic sequence;
configuring, with a processor, a variant calling module to identify variants associated with the input sequencing data in accordance with at least one characteristic of said first set of characteristics; and
identifying genomic variants, with the variant calling module processor, in the aligned genomic sequence.

18. The computer-implemented method of claim 17, further comprising:
appending a laboratory information database, via the processor, with the target enrichment technology identifier, the sequencing technology identifier, and the genomic context identifier for each of the plurality of sourcing laboratories.

19. The computer-implemented method of claim 18, further comprising:
updating the laboratory information database, via the processor, upon registration of a new sourcing laboratory; and
updating the laboratory information database, via the processor, upon update of an already registered sourcing laboratory.

* * * * *